United States Patent
Baaske et al.

(10) Patent No.: US 10,545,081 B2
(45) Date of Patent: Jan. 28, 2020

(54) SYSTEM AND METHOD FOR THE OPTICAL MEASUREMENT OF STABILITY AND AGGREGATION OF PARTICLES

(71) Applicant: NanoTemper Technologies GmbH, München (DE)

(72) Inventors: Philipp Baaske, München (DE); Stefan Duhr, München (DE); Dennis Breitsprecher, München (DE); Jonathan Derix, Unterschleißheim (DE)

(73) Assignee: NANOTEMPER TECHNOLOGIES GMBH, München (DE)

( * ) Notice: Subject to any disclaimer, the term of this patent is extended or adjusted under 35 U.S.C. 154(b) by 0 days.

(21) Appl. No.: 15/765,019

(22) PCT Filed: Sep. 30, 2016

(86) PCT No.: PCT/EP2016/073471
§ 371 (c)(1),
(2) Date: Mar. 30, 2018

(87) PCT Pub. No.: WO2017/055583
PCT Pub. Date: Apr. 6, 2017

(65) Prior Publication Data
US 2018/0284002 A1    Oct. 4, 2018

(30) Foreign Application Priority Data
Oct. 1, 2015   (EP) .................................... 15188017

(51) Int. Cl.
*G01N 15/00* (2006.01)
*G01N 21/51* (2006.01)
*G01N 21/64* (2006.01)

(52) U.S. Cl.
CPC ............. *G01N 15/00* (2013.01); *G01N 21/51* (2013.01); *G01N 21/645* (2013.01); *G01N 2015/0092* (2013.01); *G01N 2021/6482* (2013.01)

(58) Field of Classification Search
CPC ...... G01N 15/00; G01N 21/645; G01N 21/51; G01N 21/64; G01N 2021/6482; G01N 2021/6491; G01N 2015/0092
(Continued)

(56) References Cited

U.S. PATENT DOCUMENTS 9,389,211 B2    7/2016    Duhr et al.
2010/0315635 A1  12/2010   Janzen et al.
(Continued)

FOREIGN PATENT DOCUMENTS

DE    10 2007 031 244 B3    1/2009
EP        0 029 662 A1       6/1981
(Continued)

OTHER PUBLICATIONS

International Search Report (including English translation) and Written Opinion for International Application No. PCT/EP2016/073471, dated Jan. 31, 2017, 19 pages.
(Continued)

*Primary Examiner* — David P Porta
*Assistant Examiner* — Meenakshi S Sahu
(74) *Attorney, Agent, or Firm* — Westman, Champlin & Koehler, P.A.

(57) ABSTRACT

The present invention relates to a method for the optical measurement of at least the stability and the aggregation of particles in a liquid sample which is located in a sample container, wherein the method comprises the following steps: irradiating the sample with light of at least one first wavelength in order to fluorescently excite the particles,
(Continued)

irradiating the sample with light of at least one second wavelength in order to examine the scattering of the particles, measuring the fluorescence light which is emitted by the sample; and measuring the extinction light at the second wavelength, wherein the irradiated light of the second wavelength runs through the sample container, is reflected back, runs again through the sample container in the opposite direction and exits as extinction light, wherein the stability is determined based on the measured fluorescence light and the aggregation is measured based on the measured extinction light. The invention further relates to a corresponding apparatus.

23 Claims, 15 Drawing Sheets

(58) Field of Classification Search
USPC .................................................. 250/459.1
See application file for complete search history.

(56) References Cited

U.S. PATENT DOCUMENTS

2014/0234865 A1* 8/2014 Gabriel ............. G01N 15/1459
435/7.21

2015/0137005 A1* 5/2015 Baaske ................... B01L 9/065
250/453.11

FOREIGN PATENT DOCUMENTS

| EP | 0 720 747 A1 | 7/1996 |
| EP | 2 572 787 A1 | 3/2013 |
| EP | 2 848 310 A1 | 3/2015 |
| WO | 95/08774 A3 | 6/1995 |

OTHER PUBLICATIONS

A.S.G. Curtis: "Effect of pH and Temperature on Cell Re-aggregation", Nature, vol. 200, No. 4912, Dec. 21, 1963 (Dec. 12, 1963), pp. 1235-1236, XP055337464, United Kingdom, ISSN: 0028-0836, DOI: 10.1038/2001235b0, the whole document, 2 pages.
Static Light Scattering, LSinstruments, https://www.lsinstruments.ch/technology/static_light_scattering_sls/, © 2018 LS Instruments, mirusys® CMS, 2 pages, downloaded Mar. 29, 2018.
Wikipedia, Exteinktion (Optik), https://de.wikipedia.org/wiki/Extinktion_(Optik), downloaded Mar. 29, 2018., 2 pages.
NanoTemper Technology: Learn about the handling of NT.115, http://www.youtube.com/watch?v=rCot5Nfi_Og, downloaded Mar. 29, 2018, 25 pages.

* cited by examiner

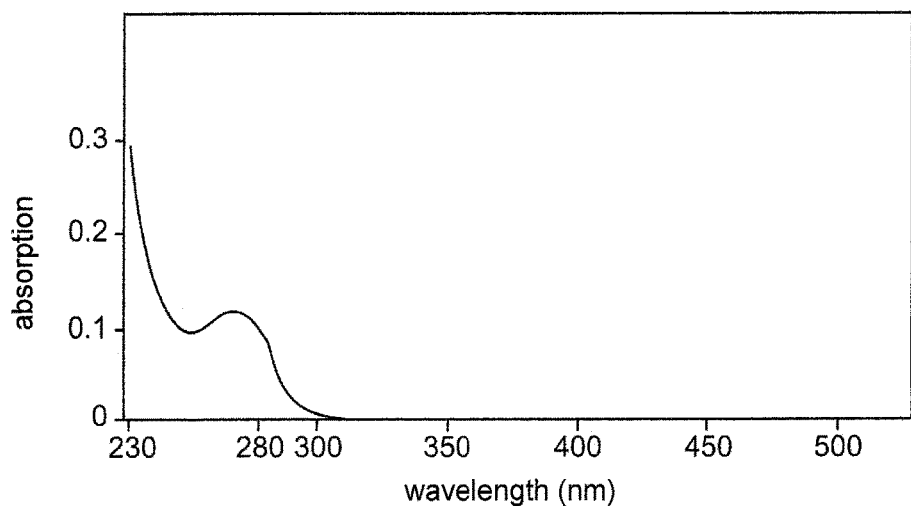
Fig. 16
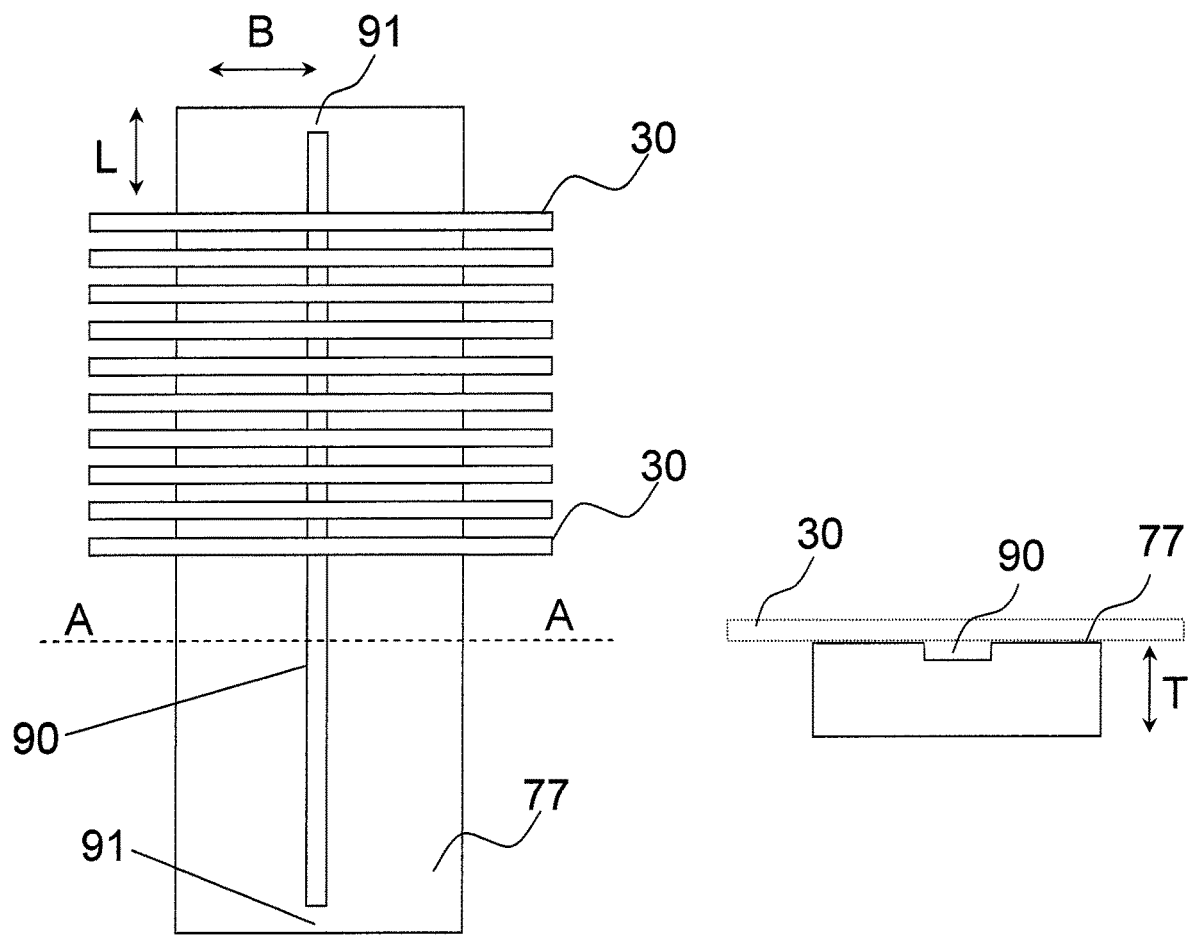
Fig. 17aFig. 17b

SYSTEM AND METHOD FOR THE OPTICAL MEASUREMENT OF STABILITY AND AGGREGATION OF PARTICLES

CROSS-REFERENCE TO RELATED APPLICATION

This Application is a Section 371 National Stage Application of International Application No. PCT/EP2016/073471, filed 30 Sep. 2016 and published as WO 2017/055583 A1 on 6 Apr. 2017, in German, the contents of which are hereby incorporated by reference in their entirety.

The invention generally relates to an apparatus or a system and a method for the optical measurement of the stability of particles. In particular, the invention relates to a system and a method by means of which not only the stability of particles but also the aggregation of particles can be measured optically. According to the invention, preferably the stability and aggregation of the particles may be measured with one single apparatus, preferably simultaneously or almost simultaneously.

BACKGROUND OF THE INVENTION

Since active agents, like for example antibodies, have been developed so as to be active only in their native form, denatured active agents are often not effective and have to be avoided. Denaturation means a structural transformation of the biomolecules, for example proteins, which in most cases is connected with a loss of the biological function of said molecules. Denaturation may be the consequence of either physical or chemical influences. Thus, active agent formulations have to be developed which prevent the denaturation of drugs, i.e. stabilize them for example thermally, chemically and/or with respect to time.

Aggregating active agents may lead to ineffectiveness as well. Furthermore, aggregated and/or denatured particles, for example aggregated antibodies, may provoke a reaction of the immune system in the body and thus have to be either avoided in drugs or their percentage in the drug has to be minimized.

Denaturation of particles, for example antibodies, has per se to be avoided since it reduces the effectiveness. The aggregation of particles, for example antibodies, has per se to be avoided since it provokes a reaction of the immune system and may also lead to a reduction of effectiveness.

It is often unclear why a particle aggregates and/or denatures: Does a particle aggregate because it denatures, i.e. because it is not in its native form or does it aggregate in its native form and denatures afterwards? Thus, in order to comprehensively characterize the particles, it is often not sufficient to analyze merely the aggregation or merely the denaturation separately from each other.

With the inventive system and method the denaturation as well as the aggregation of particles may be measured. In particular, with the inventive system and method, the denaturation as well as the aggregation of particles may be measured virtually simultaneously (substantially simultaneously) or simultaneously.

The denaturation of particles is an "intra particle" procedure and may be measured with the inventive method and system by means of measuring the intrinsic particle fluorescence (for example tryptophan fluorescence, tyrosine fluorescence). Simultaneously, the aggregation of the particles, an "inter particle" procedure which changes the size of the particles, may be measured by means of scattering of unabsorbed light.

Since the scattering of light, for example the static scattering of light in the case of the Rayleigh scattering, depends on the sixth power of the size of the particle (radius), it is very suitable to measure the changes the particle size and thus the aggregation of particles. Said light scattering method is known and is used by many apparatuses and methods. In particular, the devices known from the prior art measure the scattered light of the particles at determined solid angles, i.e. the share of light which is scattered by a particle in a determined solid angle vis-à-vis the incident light. The larger the particles and the smaller the wavelength, the larger the intensity of the scattered light for a fixed, suitably determined angle becomes (cf. for example http://www.lsinstruments.ch/technolgy/static_light_scattering_sls/). Such a method is described for example in the application US 2014/0234865 A1.

From an increase in the scattered light, for example during increase in the temperature, these methods may conclude an amendment in size and thus aggregation of the particles. A person skilled in the field of light scattering procedures knows that it has to be avoided that the excitation light which is beamed onto particles to be examined gets into the detection optics. A skilled person will always construct corresponding apparatuses in such a manner that a direct detection of said excitation light is avoided or the excitation light is blocked, which requires significant technical effort. It is for example described in patent DE 10 2007 031 244 that reflections are undesired with respect to scattering light measurements and also reflections at glass cuvettes may lead to problems.

Thus, there is the need for an improved or alternative system or an improved or alternative method for measuring the stability and the aggregation of particles.

SUMMARY OF THE INVENTION

The inventive apparatus and the inventive method are defined by the features of the independent claims. Advantageous embodiments can be taken from the subclaims.

The invention relates to a method for optically measuring or determining the stability and/or aggregation of particles in a liquid sample which is located in a sample container. According to the invention, aggregation may be measured independently of stability; preferably, however, aggregation as well as stability are determined. The inventive method comprises at least one of the following steps.

The sample is irradiated with light or a light ray of a first wavelength, in particular in order to stimulate the particles to fluorescence. The light of the first wavelength is thus a fluorescence excitation light. In order to determine the fluorescence of a sample the fluorescent light which is emitted by the sample is measured. Typically, the wavelength of the fluorescent light differs from the first wavelength of the fluorescent excitation light. Based on the measured brightness or intensity of the fluorescent light, information about the stability of the particles may be given. Preferably, the detector measures the fluorescence with fluorescent excitation light in a wavelength range from 260 nm to 300 nm, further preferably in a wavelength range from 270 nm to 290 nm and the fluorescent emission light in a wavelength range from 320 nm to 380 nm.

The aggregation of particles is determined by irradiating the sample with light of a second wavelength, preferably with a first intensity $I_0$. According to the invention, a first or second wavelength may correspond to an exact wavelength as it is provided for example by a laser. According to the invention, the term first and second wavelength may also be a "medium" wavelength or "central" wavelength, i.e. in the sense of a wavelength range. For example, wavelength ranges are emitted by a light source if the light source is not a laser. According to the invention, preferably LEDs are used which emit light over a small or large wavelength range. In order to limit the range of the wavelength, a band-pass filter="excitation filter" is preferably incorporated into the path of rays. For example, a band-pass filter may have a band-pass width between 30 nm and 1 nm in order to maintain the desired excitation wavelength range. This is particularly preferred with respect to fluorescence so that light which is emitted by the LED is limited to a wavelength range which is not in the wavelength range of the fluorescence emission detection. Furthermore, it is also preferred to use an LED for the extinction measurement. Also in this case a band-pass filter having a suitable band-pass width may be used analogously in order to limit the wavelength range which is emitted onto the sample to a "second wavelength" (second wavelength range).

The scattering of the particles is preferably determined with the second wavelength. According to the invention, the extinction light is measured at the second wavelength wherein the ratio of the irradiated light $I_0$ of the second wavelength, which runs through the sample container, and the emergent light I (intensity I), preferably also at the second wavelength, describes the extinction. Preferably, the entering radiation $I_0$ runs through the sample container, is reflected, runs through the sample container substantially opposite to the entering direction and subsequently exits as light I which is also referred to as extinction light in the sense of the present invention. Based on the measured brightness or intensity I of the exiting light (extinction light), in particular in relation to the intensity of the irradiated light information about the stability of the particles may be obtained. According to the invention, a pure aggregation measurement may be conducted also without the above-identified fluorescence measurement.

Preferably, the second wavelength is chosen such that the particles in the sample to be examined are not absorbed or only very slightly absorbed at said wavelength, preferably less than 10%, further preferred less than 5%, further preferred less than 4%, 3%, 2% or 1%. Further preferred less than 0.1%. Furthermore, it is preferred that the wavelength is chosen with respect to the absorption behavior of the particles and not with respect to the complete "sample" or "sample liquid", since possibly additions in the sample or sample liquid are present which absorb with respect to the liquid chosen. However, since the invention examines stability and aggregation of the particles, the absorption behavior of the remaining components may be assumed to be "constant".

For example, it is known that proteins absorb light in the range between 200 nm to 300 nm because of their peptide bonds (maximum of absorption at approximately 220 nm) and their amino acids (maximum of absorption at approximately 280 nm). Thus, according to the invention, preferably light having a wavelength larger than 300 nm is used (cf. FIG. 16). Preferably, the first and the second wavelengths are different. Alternatively, the first and the second wavelengths may be also equal.

In order to measure fluorescence, at least one first wavelength is used. According to the invention, it is also possible that for the fluorescence measurement a further wavelength is used in addition to the first wavelength. Thus, for example a first fluorescence may be excited at a wavelength of 280 nm and a second fluorescence at a second fluorescence channel at 632 nm.

Correspondingly, according to the invention, at least one second wavelength may be used for measuring the extinction. For example, extinction may be measured at two different wavelengths; for example at 385 nm and 532 nm. Here, it is for example possible to form and evaluate a ratio of the measured values at both wavelengths, in order to quantify for example the Mie scattering.

In other words, according to the invention it is possible to use two or more fluorescence channels and/or two or more extinction channels for determination. Preferred embodiments of the present invention or preferred feature combinations of the present invention are described in the following exemplary aspects:

1a. Method for the optical measurement, in particular of the stability and/or the aggregation of particles, ligands and/or particle-ligand complexes in a liquid sample, which is located in a sample container. Preferably, the sample container is arranged on a reflecting surface, wherein the sample container is at least partially in contact with the surface.

1b. The method according to any one of the preceding aspects preferably comprises the step of: irradiating the sample with light of at least one first wavelength, or at least one first wavelength range, to fluorescently excite the particles, 1c. The method according to any one of the preceding aspects preferably comprises the step of: irradiating the sample with light of at least one second wavelength or at least one second wavelength range to examine the scattering of the particles and/or a ligand bonding.

1d. The method according to any one of the preceding aspects preferably comprises the step of: measuring the fluorescence light emitted by the sample.

1e. The method according to any one of the preceding aspects preferably comprises the step of: measuring the extinction light at the at least one second wavelength or in the at least one second wavelength range.

1f. The method according to the preceding aspect,
wherein the irradiated light of the at least one second wavelength or the at least one second wavelength range is irradiated into the sample container such that it at least partially runs through the sample container, is reflected back by the surface, runs again at least partially through the sample container in substantially opposite direction and exits as extinction light.

1g. The method according to any one of the preceding aspects preferably comprises the step of
determining the stability on the basis of the measured fluorescence light and/or the aggregation and/or the ligand bonding on the basis of the measured extinction light.

2. The method according to aspect 1, wherein the fluorescence light and the extinction light are measured with a common optical system.

3. The method according to any one of aspects 1 or 2, wherein the irradiation of the sample with the first and second wavelength is not conducted simultaneously; or the irradiation with the second wavelength is conducted continuously, whereas the irradiation with the first wavelength is conducted intermittently, preferably periodically.

4. The method according to any one of the preceding aspects, wherein the fluorescence light and the extinction light are measured sequentially, almost simultaneously and/or emitted. Almost simultaneously is preferably within 4 ms, 2 ms or 1 ms at most. For example, only the light of the first wavelength may be switched on for 1 ms and subsequently the light of the second wavelength may be switched on for 1 ms so that almost simultaneously means within 2 ms. According to the invention, simultaneously is preferred. A simultaneous measurement may for example be achieved with the configuration of FIG. 8. The simultaneous measurement has the particular advantage of higher efficiency or performance. Thus, with the configuration of FIG. 8, for example, when measuring aggregation, a 5 times higher performance is possible than with FIG. 7.

5. The method according to any one of the preceding aspects, wherein the extinction light and the fluorescence light are measured by a common detector (cf. for example FIG. 6); the extinction light is measured by a first detector and/or a second detector, and fluorescence light of a first fluorescence wavelength is measured by a first detector and fluorescence light of a second fluorescence wavelength is measured by a second detector (51) (cf. for example FIG. 7); or the extinction light is measured by a first detector, fluorescence light of a first fluorescence wavelength is measured by a second detector and fluorescence light of a second fluorescence wavelength is measured by a third detector (cf. for example FIG. 8).

6. The method according to any one of the preceding aspects wherein the sample container is a capillary.

7. The method according to any one of the preceding aspects, wherein the sample container is tempered (heated or cooled), preferably rests on a tempering element (heating or cooling element) and is tempered by contact, wherein the tempering element preferably comprises a reflecting surface and preferably reflects back the irradiated light of the second wavelength, again runs through the sample container (30) in opposite direction and exits as extinction light.

8. The method according to aspect 7, wherein the tempering element is made of a material which has little autofluorescence. Preferably, the material has an autofluorescence of less than 5%, 3%, further preferred of less than 1%, further preferred less than 0.5% of the maximum fluorescence signal. In other words, for example if an excitation LED with maximum output emitted light and a fluorescence detector measured a maximum of 100 signals (before it saturates), merely a signal strength of 1 may be traced back to the autofluorescent material; this would be 1%. It is further advantageous when the material has a high reflectivity in the wavelength range of the second wavelength, preferably >30%, preferably >40%, further preferably >50%. Preferably, the material contains silicon or consists of pure silicon.

According to a further preferred embodiment, the surface has at least one recess, for example the form of a furrow, groove, or micro groove which extends over at least a region of the surface of the tempering element on which the capillary rests during the measurement. Preferably, the capillary is in direct contact with the surface of the tempering element during the measurement, whereas the capillary lies above the groove due to the depth of the groove and is not in direct contact with the bottom of the groove. Preferably, the groove is between 1-10 mm, more preferred between 2-8 mm, further preferred between 3-7 mm, further preferred approximately 3 mm wide, wherein the inventive back reflection of the light is preferably produced or measured in the region of the capillaries which lies above the groove. Preferably, the groove has a depth of approximately 10-30 μm. In particular, the groove has a depth of more than half of the coherence length of the used light in order to further suppress interference effects in the back scattering. Hence, preferably used LED light sources have coherence wavelengths in the range of approximately 15 μm so that a depth of the groove of >7.5 μm is preferred.

In order to guarantee an efficient back reflection of the light from the bottom of the groove, the groove is preferably etched. Preferably, the groove or the bottom of the groove has an average roughness which is preferably in the nanometer range, for example ±5 nm, preferably ±1 nm. According to a preferred embodiment, the groove may extend over a substantial part of the surface so that for example several capillaries may be arranged above the groove. According to a further preferred embodiment, the groove does not extend until the edge of the surface so that the silicon has a constant thickness around the groove and may thus be easier processed, for example by cutting or sawing.

9. The method according to any one of the preceding claims, wherein the sample container is shifted during a measurement period relatively to the irradiated light of the first and/or second wavelength and/or to the detector, is preferably run back and forth several times (continuously) and further preferably a plurality of sample containers or a plurality of capillaries are scanned by said relative movement.

10. The method according to aspect 9, wherein a fluorescence value is determined by integrating the intensity of the fluorescence light via the shifting and/or an extinction value is determined by integrating the intensity of the extinction light via the shifting.

11. The method according to any one of the preceding aspects, wherein during a measuring period, in order to determine the thermal stability, the temperature of the samples is changed, preferably increased; in order to determine chemical stability, the concentration of denaturants in different liquid samples is chosen differently; and/or in order to determine stability in terms of time, the sample is kept at a substantially constant temperature for a time period of more than one hour.

12. The method according to aspect 11, wherein during a measuring period a plurality of sample containers and/or the optical system are continuously run back and forth several times and the measurements of the fluorescence light and/or the extinction light are conducted during the movement.

13. The method according to any one of the preceding aspects, wherein the second wavelength is chosen such that less than 1%, 0.1%, 0.05%, preferably less than 0.1%, is absorbed by the sample or the particles in the sample so that the measurement of the extinction light is a direct rate for the scattering of the light of the second wavelength.

14. The method according to any one of the preceding claims, wherein the light of the first wavelength and the light of the second wavelength are united to a collinear ray which is irradiated into the sample container.

15. The method according to any one of the preceding claims, wherein the extinction light of the second wavelength, which is reflected back and leaves the sample container in the opposite direction to the irradiation direction, deviates from the irradiation direction 5° at most, preferably less than 2°, further preferred less than 1°.

16.a An apparatus for the optical measurement, in particular of the stability and/or the aggregation of particles and/or ligands and/or particle ligand complexes in a liquid sample, which is located in a sample container, in particular according to any one of the preceding aspects.

16.b The apparatus according to any one of the preceding aspects, wherein the apparatus comprises: at least one first light source for irradiating light of at least a first wavelength into the sample container, in particular in order to fluorescently excite the particles to be examined 16.c The apparatus according to any one of the preceding aspects, wherein the apparatus comprises at least one second light source for irradiating light of at least one second wavelength into the sample container, in order to measure the scattering or aggregation of the particles and/or ligand bonding.

16.d The apparatus according to any one of the preceding aspects, wherein the apparatus comprises at least a first detector for measuring the excited fluorescence light which is radiated from the sample.

16.e The apparatus according to any one of the preceding aspects, wherein the apparatus comprises at least one second detector for measuring extinction light at the at least one second wavelength wherein the irradiated light of the second wavelength runs through the sample container, is reflected back, runs again through the sample container in the opposite direction and exits as extinction light.

16.f The apparatus according to any one of the preceding aspects, wherein the apparatus comprises an evaluation means which determines the stability of the particles based on the measured fluorescence light and which determines the aggregation of the particles and/or ligand bonding based on the measured extinction light. Preferably, the apparatus comprises a first and/or second bandpass filter to narrow down the emitted light of the first and second light sources to the first and second wavelength, respectively. Preferably, a bandpass filter has a bandpass width of 10 nm, 20 nm or 30 nm.

Preferably, the apparatus has a tempering element with a reflecting surface at which the irradiated light of the second wavelength is reflected back. For example, it came apparent that silicon is particularly preferred since it has a preferred reflection behaviour and is suitable for the tempering via contact. Further, it is preferred that the apparatus is suitable to arrange at least one sample container on the surface for measurement purposes. For example, several sample containers in the form of separately arranged capillaries or by means of a carrier which comprises a plurality of capillaries may be arranged on the surface. Preferably, at least one groove is configured in the surface of the tempering element, wherein the sample container may be arranged above the groove in such a way that the irradiated light of the second wavelength is preferably reflected back at least from the bottom of the groove. For example, a groove having a width of between 1-10 mm and a depth of more than half of the coherence length of the light of the second wavelength may be configured.

17. Use of an apparatus according to aspect 16 for conducting a method according to any one of aspects 1 to 15.

The inventive method or inventive system has a completely different approach compared to conventional light scattering measurements. According to the invention, preferably the light which is not scattered is measured. Furthermore, preferably light having a wavelength which is not absorbed by the particles is used. That means the measured signal decreases when the scattering increases due to an increase in the size of the particles. Said inventive measurement technique is preferably combined with specific fluorescence optics which preferably enable a faster, more precise and more rugged simultaneous detection of aggregation (by extinction) and detection of denaturation or unfolding of proteins (by fluorescence) in high output.

The inventive method is preferably configured in a manner that the excitation light for the aggregation measurement runs through the sample container twice and is reflected back to the detector (cf. FIG. 1). According to the invention, it is also possible that the excitation light for the aggregation measurement runs through the sample container only once and subsequently the one way transmission is measured. Direct transmission as well as transmission after reflection mean that a "residuary portion" of the excitation light is measured, i.e., exactly what should have been avoided in the known methods.

According to the invention, in principle extinction is measured (cf. for example https://de.wikipedia.org/wiki/Extinktion_(Optik)). In optics, the extinction or optical density is the perceptional logarithmically formulated opacity O and thus a rate for the dilution of a radiation (for example light) after a medium has been run through. $I_0$ being the incoming radiation and I being the exiting radiation, extinction E describes the transmission degree $\tau$ as logarithmic value:

$$E_\lambda = -\log_{10}\frac{I}{I_0} = \log_{10}\frac{I_0}{I} = \log_{10}\frac{1}{\tau_\lambda} = \log_{10}O_\lambda$$

Generally, the processes of absorption, scattering, deflection and reflection are involved in dilution/extinction. Since, according to the invention, preferably wavelengths are used which are not absorbed by the particles to be examined (for example biomolecules) and other influencing variables as reflection and deflection are preferably kept constant, according to the invention substantially the dilution based on the pure scattering is measured.

This approach is particularly advantageous since said "scattering" measurement principle may well be integrated into a (single) optical system for measuring the intrinsic particle fluorescence. Thus, with only one optical system, the denaturation of the particles in the nm scale as well as their aggregation in the nm-μm scale may be detected or measured. Both measurements may be carried out sequentially, shortly after each other or even simultaneously, depending on the configuration.

According to the invention, the samples to be examined are examined preferably in capillaries, which additionally has the preferred advantage that the capillaries may be quickly brought in the desired measurement position, which makes it possible to analyze a plurality of samples simultaneously. Furthermore, this guarantees a high density of data points which makes it possible to precisely determine and evaluate even small signal changes, which is up to now not guaranteed by existing methods.

According to the invention, a plurality of capillaries may be laid directly onto an array element of the measurement device. According to a further embodiment, a plurality of capillaries may also be arranged on a separate array, which enables a semi-automatic or automatic filling and/or measurement.

Applicant of the present invention, NanoTemper Technologies GmbH, develops and sells measurement devices by means of which liquids within a capillary are optically examined. It is further known that an individual capillary is taken by hand, immersed into a liquid and subsequently positioned separately on an array and then pushed into the measurement device. Said method for filling separate capillaries is shown for example in a video of NanoTemper Technologies GmbH, which is published under http://www.youtube.com/watch?v=rCot5Nfi_Og. The individual filling is advantageous for certain individual samples, however, for larger amounts of samples said method needs many handling steps which cannot readily be automated.

In the application EP 2 572 787, which has been filed by the same Applicant as the present invention, capillaries are described which are kept to an array by means of magnetic forces. This, i.a., enables an easier and/or more exact positioning of the individual capillaries on the array. In other words, the individual filling of the individual capillaries is further preferred, however, the subsequent step is supported by the magnetic forces.

Finally, in the application EP 2 848 310 a separate array for capillaries is described, which enables also a semi-automatic or automatic filling and/or measurement. In particular, said arrays may also be used for the inventive method, which has the additional advantage that the plurality of capillaries may not only be efficiently filled but also scanned very fast.

In the following, some terms are defined as to how they should be understood in the context of the present application.

Particles

Particles in the context of the present application are, without being limited thereto, preferably: active agents, biomolecules in general, for example proteins, antibodies, membrane proteins, membrane receptors, peptides, nucleotides, DNA, RNA, enzymes; molecule fragments, "small molecules", sugars, organic bonds, anorganic bonds; vesicles, viruses, bacteria, cells, micelles, liposomes, tissue samples, tissue cuts, membrane preparations, microbeads and/or nanoparticles.

Fluorescence Measurement

The particle, preferably protein, may be denatured chemically or thermally and internal structural changes may be measured by intrinsic fluorescence, for example tryptophan fluorescence, tyrosine fluorescence, phenylalanine fluorescence, preferably tryptophan fluorescence in the case of proteins. Here, the structural/internal changes of the particle may be detected by means of changes in the intensity of the fluorescence or shifting of fluorescence maxima or changes in the fluorescence lifetime etc. The so-called melting point of the particle to be examined, for example protein, may also be determined in this way. The melting point is defined as the state in which the particle to be examined, for example protein, is half-folded (for example protein: in native conformation) and half-unfolded (for example protein: unstructured, denatured shape). In this context, the change in the fluorescence intensity may be determined for example depending on the temperature or the addition of a denaturant or co-factor/ligand and/or a temporal course may be recorded.

If proteins are examined, for example the tryptophan fluorescence at a wavelength of 330 nm+/−10 nm and 350 nm+/−10 nm may be measured simultaneously but spectrally separated. The quotient of the fluorescence intensity at 350 nm and the fluorescence intensity at 330 nm (F350/F330) is a preferred measured value since it depends on the internal structure or conformation changes of the particle. The fluorescence emission maximum of tryptophan, for example, shifts from short wavelengths (for example 330 nm+/−10 nm) to long wavelengths (for example 350 nm+/−10 nm) when the tryptophan gets out of its hydrophobic environment, for example inside a protein, due to unfolding of a protein, and into a hydrophilic environment, for example water. For example, the melting point may be determined from the maximum of the first derivation of the F350/F330 curve.

Extinction/Scattering Measurement

Particles in solutions are able to scatter irradiated light. Scattering in physics generally means the deflection of an object by interaction with a locally different object (scattering center). Scattering of light at the particles is thus the deflection of the irradiated (excitation) light by interaction with a particle to be examined. The scattering angle θ is defined as the angle about which the scattered light is deflected. According to the invention, scattering is meant when the light is indeed deflected, preferably about more than 1°, preferably more than 2°, 3° 4° and preferably less than 179°, 178°, 177°, 176°, measured from the course of the rays of the irradiated (excitation) light.

A distinction is made between different kinds of scattering, as for example Rayleigh scattering (particle dimensions ~1/10 of the light wavelength, i.e. particle dimensions which are small compared to the light wavelength) and Mie scattering (particle dimensions in the range of the light wavelength and larger). The extent of the scattering in a solution depends on the dimension and number of particles. Since the scattering intensity of the Rayleigh scattering with the inverse $4^{th}$ power depends on the wavelength, it is more distinct in short wavelength ranges, for example 300-400 nm, than in long wavelength ranges. The extent of the scattering may be quantified by extinction measurement, by comparing the intensity of the irradiated light to the intensity of the transmitted light. The difference corresponds to the amount of scattered light and thus serves as rate for the formation of particles or aggregation of particles.

In the case of biomolecules, for example proteins, the detection of extinction at a wavelength higher than 300 nm is advantageous. In particular, the detection of the extinction between 300 and 400 nm is advantageous and at approximately 385 nm particularly advantageous since here substantially no light is absorbed (absorption maximum of proteins is at approx. 280 nm), however, the scattering due to the dependency of the wavelength of the Rayleigh scattering is very high. For example, the use of light at 385 nm is advantageous since appropriate LEDs at the market are more efficient at said wavelength than LEDs having a significantly shorter wavelength. In particular, a strong light output is advantageous in order to detect many photons. Hence, the extinction measurement is often limited by photon noise. The signal-noise ratio of the photon noise follows a Poisson distribution, i.e. it improves with the root (number of photons).

Additionally, the above-mentioned selection of the wavelength for the extinction has further advantages. Since the light is not absorbed by the particles, the particles are not destroyed so that a "strong" light output in this wavelength range may be used. The light output of the LED for the extinction measurement is preferably in the range of higher than 100 µW, preferably in the range of higher than 1 mW. Preferably, the light output of the LED for the extinction measurement is in the range of 0.1 µW to 5 mW.

For measuring the extinction, little noise of the signal and a little drift of the excitation light source are advantageous. LEDs may be operated very stably and noise-reduced with suitable LED controllers and are thus advantageous for extinction measurements.

Since biomolecules, for example proteins, are significantly smaller than the advantageous wavelength ranges, Rayleigh scattering can be assumed. Since the Rayleigh scattering is dependent on the $6^{th}$ power of the particle diameter, changes in the size of the particle, for example due to aggregation of the particles, lead to a significant change in the scattering. Since the scattering at particles occurs in all spatial directions, it is proposed, according to the invention, to quantify the scattering or a degree of the scattering via the extinction since thus a quantification of the complete scattering is possible without being dependent on the scattering angle, contrary to conventional light scattering measurements in which scattered light is detected only in a small angular range. Furthermore, extinction measurements are less sensitive to measurement artifacts, for example reflections at boundary surfaces and contaminations as for example dust particles.

Preferred wavelengths or wavelengths ranges for extinction measurements can be derived for example from FIG. 16, in which an absorption spectrum for proteins is shown. For example, it can be derived from said spectrum that wavelengths which are larger than 280 nm, preferably larger than 300 nm, are particularly preferred.

Sample Containers

According to the invention, samples are examined which are in containers or sample containers in the form of liquids or fluids. In principle, the inventive method is not restricted to a certain kind and shape of sample containers. However, preferably capillaries are used as sample containers, which has several advantages. For example, the use of thin capillaries leads to a reduced waste of material due to the small volume. Furthermore, thin capillaries have high capillary forces in order to suck in the liquid passively, only by their capillary forces. Even highly viscous liquids may be sucked into the capillaries by the capillary forces. It is for example also possible to turn the sample to be sucked in upside down so that also gravitational forces act in the direction of the capillary forces and thus support the filling. The use of one-way capillaries avoids the cross-contamination between the individual samples. Thin capillary means that the optical path length through the capillary is small. This is advantageous for measuring also very highly concentrated solutions (high concentration of particles). According to the present invention, for example individual capillaries may be used or capillaries in arrays. Thus, it is for example possible to place an array with several capillaries on the reflecting surface, wherein the several capillaries preferably are in contact with the surface without having to remove the capillaries from the array. In other words, the capillaries may be tempered by contact with the surface via contact tempering, while the capillaries remain in the array.

Preferred arrays with capillaries are described for example in EP 2 848 310, which is incorporated herein by reference. In particular, EP 2 848 310 relates to an array for several capillaries which enables simultaneous filling of several capillaries of a microwell plate. Furthermore, EP 2 848 310 also relates to an apparatus and a method for filling, transporting and measuring liquids having volumes in the the microliter range. According to a preferred embodiment, 24 capillaries may be arranged in one array.

The liquid sample is preferably in a static, i.e. non-fluent state during the measurement within the capillaries. Preferably, during the measurement there are no flows within the capillary which go beyond the natural temperature movement and/or possible movements due to evaporation in the liquid.

The capillaries may be made of glass and/or a polymer and/or at least one of the elements of borosilicate glass, borosilicate 3.3 glass (for example DURAN-glass), quartz glass like suprasil, infrasil, synthetic fused silica, soda-lime glass, Bk-7, ASTM Type 1 Class A glass, ASTM Type 1 Class B glass. The polymers may comprise: PTFE, PMMA, Zeonor™ Zeonex™, Teflon AF, PC, PE, PET, PPS, PVDF, PFA, FEP, and/or acrylic glass.

In particular, it is preferred that at least one range of the capillaries is transparent for light having a wavelength of 200 nm to 1000 nm, preferably from 250 nm to 900 nm. Particularly preferred, but not limited thereto, said range of the capillary is also transparent for light having the following wavelength ranges: from 940 nm to 1040 nm (preferably 980 nm+/−10 nm), from 1150 nm to 1210 nm, from 1280 nm to 1600 nm (preferably 1450 nm+/−20 nm and/or 1480 nm+/−20 nm and/or 1550 nm+/−20 nm), from 1900 nm to 2000 nm (preferably 1930 nm+/−20 nm). The skilled person understands that the transparent range(s) may also extend over the complete capillary. In other words, the capillaries may be transparent and are preferably made integrally of one of the above-mentioned materials.

Preferably, the used capillaries have an inner diameter of 0.1 mm to 0.8 mm, preferably 0.2 mm to 0.6 mm, further preferably 0.5 mm. The outer diameter of preferred capillaries is preferably between 0.2 mm to 1.0 mm, preferably 0.3 mm to 0.65 mm.

The geometry of the capillaries is not limited to a certain shape. Preferably, tube-like capillaries having a round cross-section or an oval cross-section are used. However, it is also possible to use capillaries having a different cross-section, for example, triangular, quadrangular, pentagonal or polygonal. Furthermore, capillaries may be used which have a diameter and/or cross-section which is not constant or constant over the length of the capillaries.

Silicon Surface

According to the invention, the sample containers are on a silicon surface. Preferably, capillaries which are arranged above a silicon surface are used as sample containers. The silicon surface preferably serves as reflecting surface or surface for the reflection of the excitation light. Furthermore, according to the invention, the sample containers or capillaries may be brought into direct contact with the silicon surface so that a direct contact heat exchange between sample container/capillary and silicon is achieved. Silicon has some properties which are particularly advantageous for the present invention.

Silicon does not have autofluorescence in the preferred wavelength range. Silicon has a high reflection in the wavelength range which is preferred according to the invention (cf. for example FIG. 9). Furthermore, silicon has a high thermal conductivity which is particularly advantageous for the fast and homogenous tempering of a plurality of capillaries. Said three properties are particularly advantageous for the inventive apparatus and the inventive method.

Further advantages of silicon are for example its chemical resistance and that it is easily available and easy to produce, which furthermore makes it possible to form very smooth or very precise shapes/surfaces.

However, the invention is not limited to the use of silicon. Thus, other materials may be used for the reflecting surface and/or tempering instead of silicon. Generally, materials are suitable which have low autofluorescence or no autofluorescence in the preferred wavelength measurement range and preferably simultaneously show reflection of the irradiated light, for example >10% reflection. According to the invention, for example also a quartz layer or a quartz plate may be used which is preferably provided with a reflecting coating, for example an interferometric coating.

The present invention offers several advantages with respect to efficiency, speed and costs for conducting a plurality of measurements. The combination of thin capillaries which preferably rest on silicon and which are preferably continuously shifted relative to a single optical system together with the measurement of the intrinsic fluorescence (fluorescence, phosphorescence, luminescence) and the measurement of the scattering (extinction) is preferred and particularly advantageous. In particular, silicon is a preferred material due to the combination of the very good heat conducting properties and the property to reflect light of the used wavelength. The fast and precise detection of extinction by running a plurality of samples without resting on individual capillaries also drastically increases the measurement speed and data point density compared to conventional methods.

The inventive method and the inventive apparatus fundamentally differ from the prior art. In particular, according to the invention, components are combined in a way which a person skilled in the art of light scattering would not use based on the teaching of the prior art. Furthermore, the inventive measurement also differs from known methods a person skilled in the art of absorption measurements would conduct. In principle, there are commonalities between the optical system for an absorption measurement and an inventive apparatus. According to the invention, however, the wavelength for the extinction measurement is specifically directed such that it is not absorbed by the sample. Thus, according to the invention, a measurement of the scattering of the light dependent on the dimension may be achieved.

For example, from the prior art an apparatus is known which is sold under the name UNit™ by unCHAINED LABS. In said apparatus, the microcuvettes have to be controlled individually and for the measurement the microcuvettes have to be arranged exactly with respect to the measurement optics. According to the invention, the capillaries permanently/continuously move without stopping for the measurement; the capillaries are "completely scanned". Thus, according to the invention, a more robust, more efficient configuration and especially a much higher data density is achieved.

Due to the recording of complete spectra according to the prior art, the measurement time per controlled microcuvette takes several seconds. Thus, the measurement of for example 48 samples at one temperature already takes several minutes. A heating rate with the usual 1° C./min thus leads to a small data point density. According to the invention, it is already sufficient that merely two discrete wavelengths are detected (extinction and fluorescence), wherein the capillaries may be exposed to light for <50 ms each during passing by so that, according to the invention, a data point density which is by ranges higher is achieved.

In the prior art a static light scattering measured as usual, i.e. the excitation light is blocked such that indeed only a part of the light which is scattered is measured. According to the invention, however, the transmitted part or the reflected part is measured, i.e. the light or part of the irradiated light which is not scattered.

Furthermore, the measurement of the light scattering from the prior art needs an exact aiming at the samples, which requires extensive adjustment and regular maintenance. Furthermore, this leads to a poor repeatability since even small errors in aiming at separate samples may lead to fluctuations in the light scattering signal.

According to the invention, the extinction light is measured after the light has twice run through the capillary due to reflection. In the case of high concentration of the particles and a long path length (for example 1 cm), no light would return through the capillary. Thus, according to the invention, thin capillaries having an inner diameter of for example 0.5 mm are preferred. The solutions/methods/apparatuses which are presently available have problems with handling and measuring highly concentrated solutions, for example highly concentrated antibodies (for example with 150 mg/ml antibodies in aqueous solution). On the one hand since they cannot fill highly viscous liquids into the sample chambers used, on the other hand since their optical path lengths are too long. Said highly concentrated solutions are, however, very interesting for the pharmaceutical industry, in particular the formulation measurement.

The use of thin capillaries allows a large dynamic measurement range since the measurements are highly sensitive (little/no autofluorescence of the capillary material and the silicon in the case of fluorescence detection, high transmission of the thin-walled capillaries and good reflection properties/homogeneity of the silicon in the case of extinction detection), and at the same time allow the measurement of highly concentrated solutions (thin optical layer thickness advantageous with respect to extinction measurements of highly concentrated solutions). The inventive method is robust vis-à-vis inner filter effects since each individual sample is referred to itself. Thus, large ranges of material amount concentration, for example from 50 mg/ml protein to 5 µg/ml protein, may be analyzed in one single measurement.

Property: Continuous Running Back and Forth of the Capillaries Under the Optics:

The preferred continuous relative shifting of the capillaries to the optics during a measurement (cf. FIGS. 3 and 4) has further advantages with regard to efficiency and precision of measurement. According to the invention, a plurality of samples may be measured parallel, for example by tempering all samples simultaneously to the same temperature. The inventive method does not require a long residence time on the individual capillaries; a directed driving to a specific measurement point on the capillary is not needed either, due to which the method is very robust and very fast.

According to the invention, furthermore, the symmetry of the capillary may be utilized since the measurement is preferably conducted perpendicular to the longitudinal axis of the capillary. Furthermore, round or cylindrical capillaries (round cross-section) are advantageous since such capillaries cannot only be manufactured cheaply but also having a good quality and with high preciseness.

Due to the inventive fast scan procedure very high data point densities may be achieved, which has advantageous effects on the data evaluation. In the following, some of said advantages are calculated by means of an example.

For example, 48 individual capillaries having an inner diameter of 0.5 mm and an outer diameter of 0.65 mm are arranged horizontally on the tempered silicon in a distance of 2.25 mm (center of the capillary to center of the capillary). Said complete tempering body with the capillaries is continuously run back and forth under a fixedly mounted optical system, for example by means of a linear axis, which is operated for example by a step motor.

For example, the tempering body and thus the capillaries are scanned under the optics with a speed of for example 45 mm/s. At this speed, all 48 capillaries are started with a distance of 2.25 mm within approximately 3 seconds. In particular, by running back and forth, each capillary is measured every 3 seconds on average ("on average" since for example the outermost capillaries are measured twice practically instantaneously by reversing the driving direction and it thus takes 3 seconds (driving back)+3 seconds (returning)=6 seconds until the capillary is again exactly under the optics).

In an exemplary configuration the temperature of the tempering body is measured and thus the temperature of the capillaries is continuously increased by a rate of 1° C. per minute during the continuous running back and forth. Thus, with the temperature ramp of 1° C. per minute, a data density of 20 measurement points per capillary and per minute is achieved, which corresponds to a temperature definition of 0.05° C. on average. If the increasing speed of the temperature of 1° C. per minute is halved to 0.5° C. per minute with a constant number of capillaries and constant running speed, the temperature definition of 0.05° C. doubles (case 1° C. per minute) to 0.025° C. (case 0.5° C. per minute).

Since it is scanned, i.e. measured continuously over the complete diameter of the capillaries, the inventive method is more robust vis-à-vis local contaminations (for example dust particles, air bubbles, in particular contaminations which are smaller than the diameter of the capillary) than conventional methods from the prior art, according to which it is measured only at one single point of the capillary (cf. for example UNit™ by unCHAINED LABS). In particular, in the prior art already little local contaminations may lead to a measurement artifact and to a rejection of the measurement.

A further advantageous aspect of the inventive scanning of the capillaries is that different layer thicknesses are measured practically automatically due to the scanning of the round capillaries with the "measuring beam". Thus, for example FIG. 3 shows that the maximum sample thickness/layer thickness is in the center of the capillary. A smaller layer thickness of the sample liquid is symmetrically at the edges. This is for example advantageous for very highly concentrated solutions in the case of which the scattering is so high that in the center of the capillary (greatest layer thickness) no signal gets through (the complete light is scattered). However, if no signal gets through, no changes in the signal can be measured. Since, according to the invention, it is scanned over the complete diameter of the capillaries, measured values >0 are achieved in the edge regions in which the reflected ray of light had to cover a shorter distance through the capillary. This is a practical advantage since thus a higher concentration range of samples may be measured in the solution.

Optics for Measuring the Fluorescence and Extinction/Scattering

A further advantage of the present invention can be seen in the optics for measuring the fluorescence and extinction, which is constructed in a simpler manner. Advantageously, a common optical system may be used for both measurements. The advantages of the inventive (common) optics are for example in the fields of adjustment, positioning, material consumption, compared to the separate optics from the prior art. In addition, the inventive common optical system also saves space.

According to the invention, the fluorescence measurement and the extinction measurement may be conducted subsequently, almost simultaneously or simultaneously. Simultaneous measurement means: intra particle (=intramolecular) processes by means of fluorescence may be conducted simultaneously with the measurement of the particles' change in size (=intermolecular) by means of "scattering"/extinction. This leads to a direct correlation of both processes. In this way it can be recognized whether denaturation (fluorescence) and aggregation (extinction) start simultaneously or at the same temperature or whether one process starts before the other. This also leads to a more robust measurement.

The fact that the measurements are conducted simultaneously also leads to a higher or high data density: twice as much data may be measured per time unit as if extinction and fluorescence are measured separately from each other. Thus, the measurement is more precise and the melting point of a protein and the temperature at which the aggregation of the protein begins may be determined more easily.

The inventive configuration of the extinction measurement ("scattering" measurement) is more robust against contaminations, pollutions, air bubbles on and in the capillary than static scattered light measurements.

Preferred concentrations of material amounts of particles, for example proteins like antibodies, enzymes, peptides are between 0.001 and 500 mg/ml. Advantageous concentrations are between 0.1 and 100 mg/ml.

The inventive configuration and the inventive method make it possible to simultaneously measure many different concentrations in one single experiment. That means that concentrations which differ for example by the factor 1000 may be measured simultaneously with one and the same measurement setting.

By means of the inventive system and method, measurements of the thermal stability of particles, chemical stability of particles as well as stability of particles with respect to time are possible. In the following, examples for measuring the stability are described in more detail.

Thermal Stability

When thermal stability is measured, the capillaries with particles in aqueous solution or liquid phase are placed on the tempering body, which comprises silicon, are the intrinsic fluorescence and (preferably simultaneously) the scattering/extinction is preferably continuously measured while the temperature of the capillaries is increased from a low value, for example 15° C. to a high value, for example 95° C. (cf. FIG. 13). For example, temperatures of −20° C. to +130° C. and/or portions thereof may be used as well.

At first, the silicon surface is cleaned with a cloth and absolute ethanol by wiping it several times. Subsequently, at least 10 µl of the samples to be analyzed are prepared, for example antibody solutions in different concentrations of material amount, for example between 5 mg/ml and 0.3 mg/ml or different biomolecules or identical biomolecules in different buffers. 10 µl of each solution are then filled into the capillaries by means of capillary forces by immersing the capillaries into the solutions. Filled capillaries are then transferred to a capillary array and subsequently pressed onto the silicon surface by means of a lid. By means of a "discovery scan", which determines the extinction as well as the fluorescence at 330 and 350 nm emission wavelength of all capillaries within 3-5 seconds at a temperature of 20° C., the luminous intensities are adapted, which may be carried out manually or automatically in order to avoid overexposure of the detectors. Subsequently, the temperature range to be measured, for example 20° C.-95° C., and the temperature ramp, for example 1° C./min are determined. The latter one may be varied for example between 0.1° C./min and 100° C./min. After said parameters have been determined, the measurement is started and the temperature dependency of the sample extinction and sample fluorescence is simultaneously measured and displayed. After the measurement is finished, the temperature is automatically set back to the starting value.

The analysis of the thermal unfolding curves is carried out for example via the determination of the specific unfolding temperature (the temperature at which 50% of the particles are unfolded), which may be carried out for example by identification of the inflection points by analysis of the first or second derivation of the raw data or by other mathematical processes. The analysis of the particle formation by extinction measurement is preferably carried out by detecting the temperature at which the aggregation starts and by determining the maximum extinction.

For example, the reversibility or irreversibility of the unfolding of a particle may also be determined by means of a thermal stability measurement. This may be carried out for example by first increasing the temperature from 20° C. to 95° C. with a temperature ramp of 1° C. per minute and subsequently decreasing the temperature of 95° C. with the same or a different temperature ramp to 20° C. If an unfolding is reversible, for example, after the process of heating up and cooling down, the fluorescence ratio of 350 nm to 330 nm reaches again the starting level/the same value as it had for said process. With the simultaneous measurement of the aggregation, according to the invention, it may be discovered whether the aggregation leads to an irreversibility of the unfolding. For example, in case an antibody has different thermal unfolding processes in the fluorescence signal, for example with melting temperatures of 60° C. and 72° C. and in case it simultaneously has an aggregation at 75° C. during the extinction, for example it is possible to heat to 60° C. in a first experiment and then cool down again and heat to more than 75° C., i.e. beyond the aggregation temperature and then cool down again in a second experiment. If the first experiment shows a reversible unfolding and the second experiment shows an irreversible unfolding, it can be concluded that the aggregation leads to an irreversible unfolding or prevents the refolding into the native state.

Chemical Stability:

When measuring the chemical stability, particles are mixed in aqueous solutions with increasing concentrations of denaturants, for example chaotropic salts like guanidinium hydrochloride or urea and filled into capillaries and placed on the tempering body. The extent of the unfolding of particles is detected at a defined temperature by one-time running the capillaries and detecting the fluorescence (cf. FIG. 12).

Fields of use for chemical unfolding are for example the optimization of formulations of proteins, for example antibodies and enzymes, the thermodynamic characterization of particles as well as the active agent research.

Stability with Respect to Time

When measuring the stability with respect to time, particles are filled in aqueous solution into capillaries and the extinction and fluorescence are measured at constant temperature over a defined time period. With respect to measurements >3 hours it is advantageous to seal the capillary ends with suitable substances, for example liquid plastic, adhesive, wax, putty or mechanically by pressing suitable materials, for example silicone, rubber, plastic, in order to avoid loss of sample material by evaporation. Measuring the stability with respect to time is for example used for the characterization of particles, in particular proteins and active agents, and for the optimization of the formulation of said particles.

Quality Control

When measurements are carried out for the quality control, particle solutions are tested with respect to their reproducibility or storage and stress tests are conducted. With respect to the latter one, for example proteins are exposed to conditions which potentially have negative influence on their folding, for example increased temperature, intensive shaking/stirring, cycles of freezing and unfreezing. After conducting the different procedures, the solutions are filled into capillaries and the fluorescence as well as the extinction of the samples is detected either with a single capillary scan or in a temperature ramp, for example with 1° C./min from 20° C. to 95° C. By comparing to an untreated reference sample, the share of unfolded and aggregated protein may be detected.

Ligand Bonding

Said measurements are also referred to as "thermal shift assays". When measuring the ligand bonding, particles, for example enzymes, for example kinases, together with ligands, for example fragments of molecules, incubated in aqueous solution. If a ligand bonds to a particle, said ligand bonding may influence the stability, for example the thermal stability, of the particle and/or its aggregation behavior. For example, a ligand bonding to a particle may increase or decrease its melting temperature, the temperature at which 50% of the particle are in native form and 50% are in denatured form, i.e. stabilize or destabilize the particle. Said shifting of the melting temperature of the particle-ligand complex vis-à-vis the particle without ligand may be measured as "delta T" and thus the bonding of the ligand to the particle may be detected. The inventive method and apparatuses make it possible to reliably and reproducibly detect and quantify even the smallest shifting in the melting temperature of delta T>=0.2° C. Different ligands may then be assorted and selected for example by means of the shifting in their melting temperature delta T. With respect to applications as for example crystallography of proteins, ligands are searched for which shift the melting temperature of the particle to particularly high melting temperatures when bonding and thus stabilize the particle.

Here, it is advantageous to measure not only the thermal stabilization by means of fluorescence signal, but also a possible aggregation of the particles, ligands and/or particle-ligand complexes by means of the inventive extinction measurement. This should make it possible to sort out, for example, ligands which lead to a thermal stabilization as well as to an aggregation.

BRIEF DESCRIPTION OF THE DRAWINGS

In the following, preferred embodiments of the present invention are described in detail by making reference to the Figures:

FIG. 16 shows an exemplary absorption spectrum of a protein; and

FIG. 17 a, b shows a top view and cross-sectional view of an inventive tempering body.

DETAILED DESCRIPTION OF PREFERRED EMBODIMENTS

Figure 2:
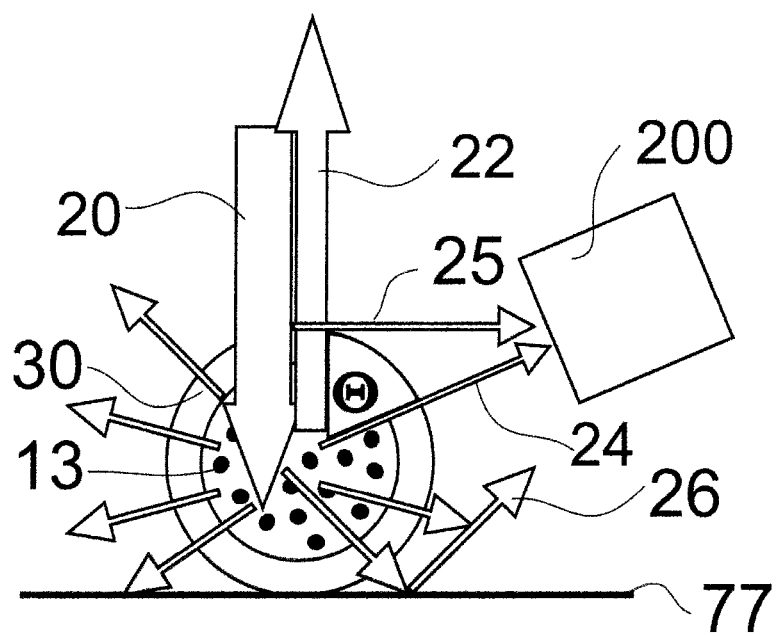
FIG. 2 shows the direct measurement of scattered light with a fixed scattered light detection angle according to the prior art.

FIG. 2 shows a usual method for measuring particles by means of a static scattered light measurement in a fixed angle. The sample 13 to be examined is a liquid with strongly scattering or strongly aggregating particles. The sample liquid is in a capillary 30, which is arranged on a surface 77. For an extinction measurement light 20 is irradiated from the top downwards through the capillary 30 into the sample liquid. One part of the irradiated light 20 is directly, i.e. substantially opposite to the irradiation direction, reflected back as reflected light 22. For the measurement of scattered light 24 a scattered light detector 200 is in an angle Φ between irradiating ray of light 20 and sample and thus directly determines the light 24 which is scattered into the sample with strongly scattering particles 13.

The disadvantages of the system may be summarized as follows. The contribution to the signal in the detector 200 is only generated by the scattering into a small angle range/range around the angle Φ. Due to the measurement in a small angle range, the system is prone to undesired mechanical movements, for example movements in the vertical direction. In certain positions of the capillary 30 reflections at the capillary walls (for example ray 25) in the direction of the detector 200 are stronger than the light scattering at the particles to be examined. A person skilled in the art of scattered light measurements knows that it is important to avoid reflections or reflecting surfaces 77 (for example silicon) since from there for example an undesired reflected ray 26 may also enter the detector 200. Said reflected ray 26, which enters the scattered light detector 200, leads to falsification of the measurement signal, since for scattered light measurements only a very small angle range around the angle Φ may be measured according to the conventional teaching. Thus, the skilled person will construct a very complex optical system in order to block all undesired scattered light, which, however, makes the optical system fragile and expensive. In particular, a skilled person will avoid reflecting surfaces. Furthermore, the inclined arrangement of the detector 200 impedes the integration in existing optics with vertical path of rays.

Figure 1:
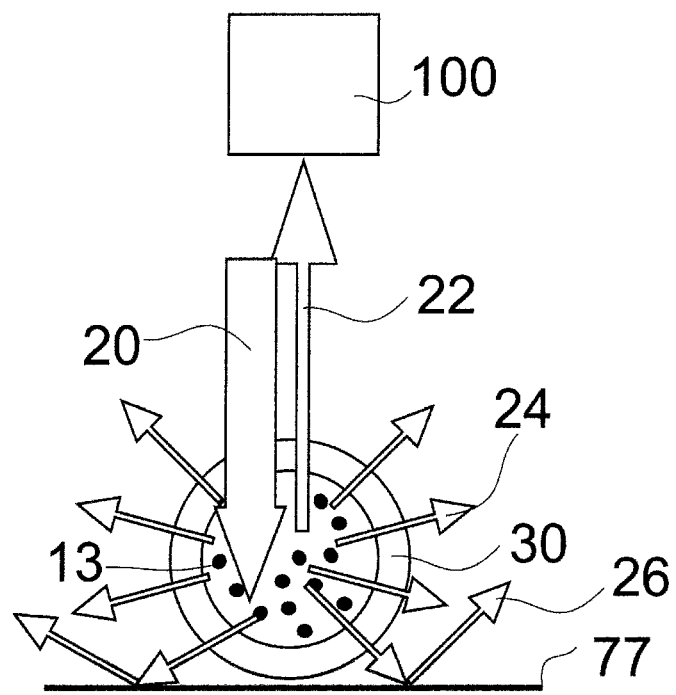
FIG. 1 shows the mode of operation of the inventive measurement of the scattering of light by measuring the dilution of the light transmission.

FIG. 1 schematically shows the mode of operation of an inventive measurement. Preferably, according to the invention, the scattered portion of light is not measured directly as in FIG. 2, but by measurement of the dilution of the light transmission, the so-called extinction. In other words, the extinction light is light which is not scattered. Dependent on the configuration of the optics, light which is scattered less than ±10°, preferably less than ±8°, 7°, 6°, 5°, 4°, 3°, 2°, 1° from the ray axis A of the irradiated light 20 is preferably interpreted as light which is not scattered. When having a high acceptance angle range, a high signal-noise-ratio may be reached, when having a small range, the linearity is better at high concentrations.

Again, in this example, the sample to be examined is in a capillary 30 which rests on a surface 77. The light of an arriving ray of light 20 is scattered by particles in the sample solution 13 partly under different angles (cf. scattered light 24). The ray of the irradiating light is reflected at the surface 77 and returns as ray of light 22 opposite to the irradiated ray of light 20. The intensity of the ray of light 20, 22 which has been reflected at the surface 77 and thus twice ran through the sample volume 13, depends on the intensity of the light scattering in the sample. The intensity of the reflected ray 22 is measured by a detector 100, whose acceptance range is collinear to the ray of light 20 or the rays of light 20, 22. The wavelength of the arriving/irradiated rays of light 20 and the reflected rays of light 22 is preferably chosen such that the sample to be measured absorbs as little light as possible in said range. Thus, it may be achieved that the dilution of the light is predominantly effected by scattering (extinction) and not by absorption. A further advantage of said inventive method is that rays 26 which are reflected at the surface 77 do not disturb the measurement.

FIG. 17a shows the surface 77 of the inventive tempering body with several capillaries 30 arranged thereon in top view. The surface 77 has a length L and width B, wherein the surface layer furthermore has a depth T, as can be seen from FIGS. 17a and 17b. Preferably, the length L is longer than the width B. Furthermore, it is preferred that for the measurement the capillaries 30 extend along the width B of the surface 77 and the capillaries are preferably longer than the width B so that both ends of the capillaries project over the surface 77. In order to temper the capillaries 30 via contact, it is preferred that the capillaries directly rest on the surface 77 of the tempering element, i.e. are in direct contact to the surface 77. According to a further preferred embodiment it may further be advantageous to configure at least one region such that a portion of the capillary is not in direct contact to the surface while other region of the capillary are in contact with the surface. In particular, a region without direct contact is advantageous for optical measurements, as will be discussed in the following.

According to a preferred embodiment a recess 90 may be provided in the surface 77, for example in the form of a furrow, groove, micro groove or "ditch" 90 so that there is no direct contact of the capillary to the surface 77 in the region of the groove 90. The groove 90 preferably extends over at least a region of the tempering element on which the capillaries rest during the measurement. The groove 90 is preferably configured in the central region with respect to the width of the tempering element so that each capillary has no direct contact to the surface 77 in a central measurement region 90. However, right and left of said region 90 (with respect to the width of the tempering element) the capillary 30, is in direct contact to the surface in order to secure a contact tempering.

The groove is preferably between 1-10 mm, more preferably between 2-8 mm, further preferably between 3-7 mm, for example 5 mm, further preferably has a width of approximately 3 mm (along the width B). According to the invention the inventive reflection of the light is produced or measured preferably in said groove portion of the capillaries.

Preferably the groove is approximately 10-30 μm deep. It is particularly preferred that the groove 90 has a depth (see direction of depth T in FIG. 17b) of more than half of the coherence length of the used light in order to further suppress interference effects in the backscattering. Disturbing interference effects for example occur due to Newton's rings which may be suppressed or even avoided with an inventive groove. According to the invention, a laser light source or an LED may be used as light source. LED light sources, as they are for example used in the present invention, typically have coherence wavelengths in the range of approximately 15 μm so that a depth of the groove of >7.5 μm is preferred. It is particularly preferred that the depth is between 1.5 times of half of the coherence wavelength and 10 times of half of the coherence wavelength. Preferably, the upper limit of the depth is 5 times of half of the coherence wavelength. In particular, according to the invention, the groove should be only deep enough to suppress interferences, in return, however, there should not be an air cushion below the capillary which is too big since in this case the desired temperature in the capillaries could be disturbed by the air cushion. Furthermore, the groove has the further preferred advantage that the surface of the capillary 30 is not in direct contact with the surface 77 so that scratching of the surface of the capillary 30 and scratching of the surface of the tempering body by the capillary may be suppressed or avoided in the measurement region (groove). In particular, according to the invention, it may be avoided that the surface of the tempering body is scratched, whereas a possible scratching of the capillaries may be tolerable since the capillaries are preferably used as disposable article. According to the invention, for example capillaries may be used whose material has a lower hardness than silicon.

In order to guarantee an more efficient reflection of light from the bottom of the groove 90, the groove is preferably etched into the surface of the tempering element. Preferably, the tempering element has a surface layer made of silicon so that the groove 90 is configured directly in the silicon layer. According to a preferred embodiment of the invention, the groove is etched into the silicon. Furthermore, the preferred etching method has the advantage that the surface of the bottom of the groove is configured in a very smooth way so that the reflection behavior of said surface is still excellent. Preferably, the surface of the bottom has an average roughness which is preferably in the nanometer range, preferably <±10 nm, preferably <±5 nm, for example ±1-2 nm.

According to a preferred embodiment, the groove may extend over a substantial part of the surface so that for example all capillaries 30 which have to be measured and rest on the surface 77 may be arranged above the groove 90. As illustrated in FIG. 17a, the groove 90 extends along the length L so that the capillaries 30 may be arranged transversely over the groove 90 (cf. FIG. 17b). According to a further preferred embodiment, the groove 90 does not extend over the complete length L so that preferably in the edge region 91 no groove is configured. This has, for example, the advantage that the silicon has a constant thickness around the groove 90 and may thus be easier processed (for example cutting or sawing).

Preferably, silicon is used as surface of the tempering element. Preferably, pure (crystalline) silicon is used, as discussed in detail further below. Preferably, the inventive groove 90 is configured along a preferred crystallographic direction of the crystalline silicon, preferably along the [111] direction (Miller's direction indices).

For example, the groove also has the advantage that liquid which is at the outside of the capillary does not reach the measurement region which is preferably in the region of the groove. Since in the region of the groove the distance between capillary and tempering body is larger than outside the region of the groove, it is favorable that the liquid at the outside of the capillary stays outside the groove because of the capillary forces.

Thus, it may happen, for example, that when the capillaries are filled sometimes droplets stick at the outside of the capillary. Said droplets may disturb when they reach the measurement region. However, the capillary forces, which are greater the smaller the distance from capillary to tempering body is, hold said liquid outside the groove. Thus, it may, for example, be avoided that the liquid of the droplets reach the measurement region in the groove.

FIGS. 3a) to 3c) show the development of the signals for an inventive fluorescence measurement and extinction measurement. Similar to FIG. 1, the sample to be examined is in a capillary. The sample to be examined contains scattering/aggregating particles (in the following referred to as sample 12) as well as fluorescent particles (in the following referred to as sample 15). In order to measure the sample, preferably the detector is shifted above the capillary or the capillary is shifted below the detector. Said shifting is conducted preferably transversely to the longitudinal axis of the capillary. Alternatively, capillary as well as detector may be shifted. However, preferably a relative movement 80 between capillary 30 and detector 100 is supposed to happen during a measurement.

Before a capillary 30 is reached by the irradiated rays of light for the fluorescence measurement and extinction measurement 20, 21, the detector does not measure a fluorescence light 23 (upper row; signal (fluorescence)) and no dilution in the reflected light 22 for the extinction measurement 22 (lower row; signal (extinction)). Correspondingly, a horizontal line is shown in the diagrams in FIG. 3a.

During the (relative) movement 80 of the capillary 30 under the detection region of the optical system, the measured fluorescence intensity 23 increases and the intensity of the reflected ray 22 decreases by refraction at the capillary and by scattering in the sample 12 (cf. FIG. 3b).

When the capillary with the sample leaves the detection region of the optics, preferably signals are generated which correspond to the signals which are generated when driving into the detection range. This is caused by the symmetrical arrangement of the optical system or the symmetrical movement above the capillary. Thus, the direction 80 of the movement between samples and optical system is irrelevant.

According to the invention, a plurality of samples which are in a plurality of capillaries may be measured continuously after each other. The plurality of capillaries may be arranged preferably on a sample array. That means by a preferably continuous movement of a sample array a plurality of samples with high data density (data points per sample per time unit) may be recorded. Thus, it is for example possible to obtain measurement frequencies up to more than 100 kHz. A further advantage of said inventive method is the low adjustment effort of the system. Furthermore, capillaries 30 as format for a sample chamber make simple filling possible by automatically filling the sample into the capillary by capillary forces, which for example also makes it possible to fill in highly viscous solutions. The capillaries preferably directly rest on the surface 77 and have good heat contact.

Figure 4:
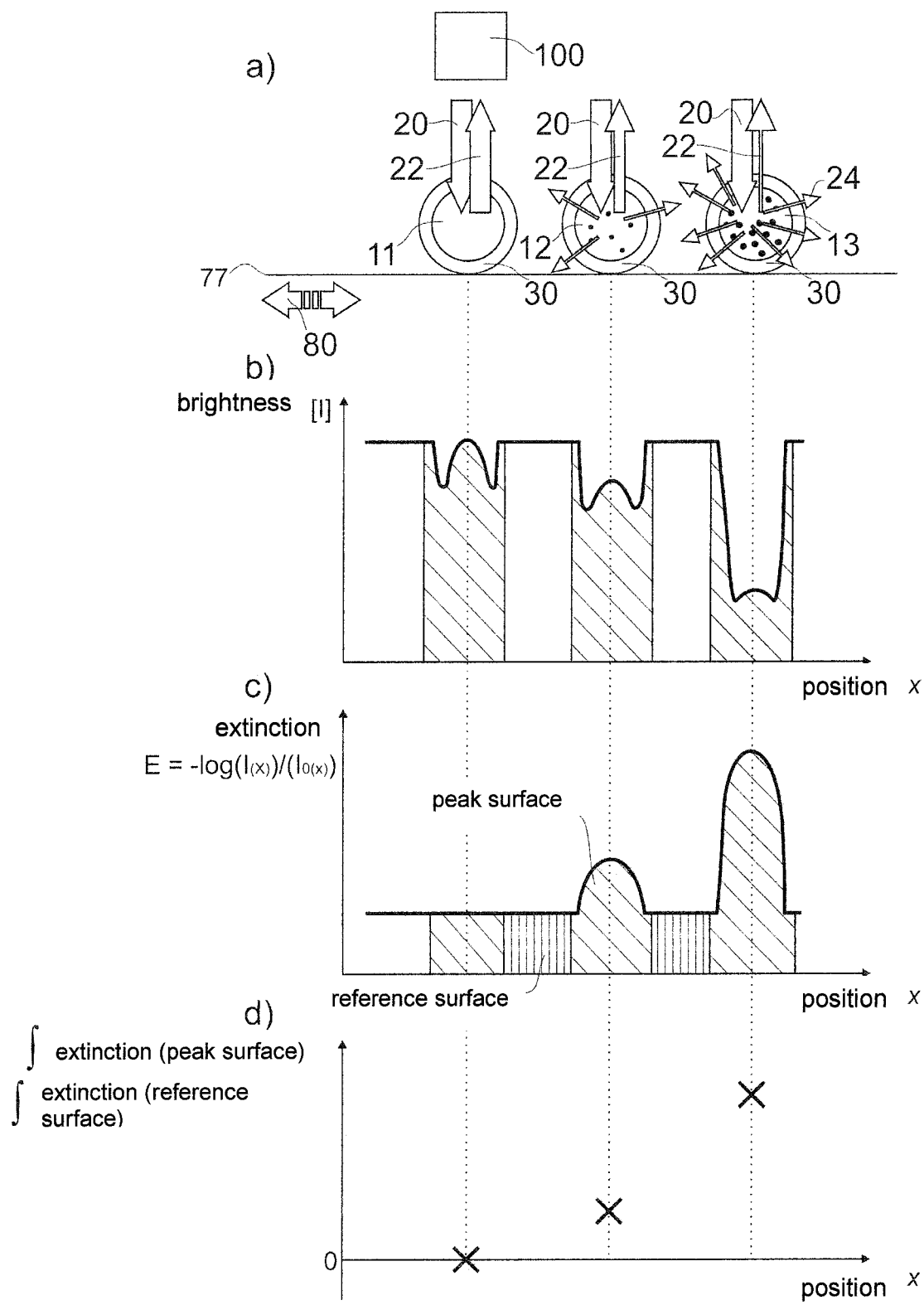
FIG. 4 shows an embodiment for evaluating the extinction measurement.

FIG. 4*a*) shows a cross-section through three different samples 11, 12, 13 in capillaries 30. The first sample 11 does not scatter the light 20 produced and emitted by a source so that the largest portion 22 of the irradiated light rays 20 is reflected back in the direction of the objective lens and detector 100. The other two samples 12 and 13 scatter a portion of the irradiating light 20 in different directions outside the acceptance angle of the detector 100. A larger part of the irradiating light is scattered through the sample 13 than through the sample 12, which is shown by the plurality of scattering arrows 24.

Figure 3:
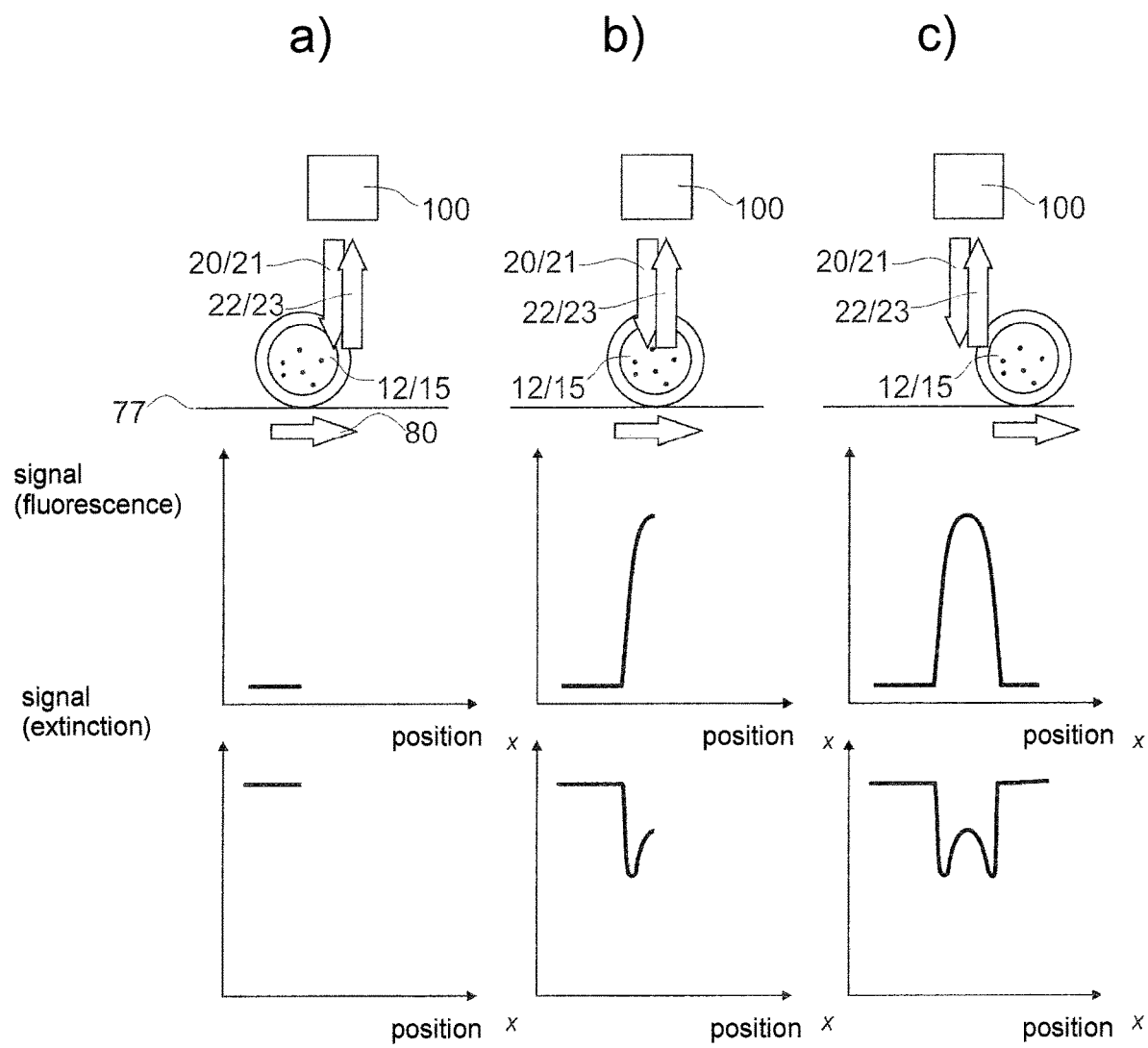
FIG. 3 shows the development of fluorescence signals and extinction signals by moving the samples relative to the optical system.

As already described with respect to FIG. 3, it is preferred that during a measurement the samples are moved relatively to the optical system. FIG. 4*b*) shows a typical course of the light intensity measured by the detector 100 dependent on the horizontal position of the samples (extinction measurement). The measured intensity (brightness [I]) depends on the one hand on the light diffraction at the capillary walls 30 and on the other hand on the extinction in the sample. The light diffraction at the capillary walls may be assumed to be identical in a good approximation in different samples. Since the samples 12 and 13, however, scatter a larger portion of the irradiating light 20 than the sample 11, less light 22 is reflected back. Thus, the brightness (intensity) in samples 12 and 13 decreases to a greater extent.

FIG. 4*c*) shows a possible course of the extinction dependent on the position of the samples. The formula for calculating the extinction generally is $$E(x) = -\log\left(\frac{I(x)}{I_0(x)}\right)$$

I0(x) may be a constant in the simplest case or the course of intensity in a capillary filled with water or the course of intensity when a measurement is started before the extinction has started because of temperature-induced formation of aggregation.

The desired measurement value "extinction" (FIG. 4*d*) results from integration of the extinction course E(x). The integration limits are preferably symmetrical around each capillary. In order to balance fluctuations of the brightness of the light source or the sensitivity of the detector, the detected extinction may be corrected by a reference value which is calculated by integration of the curve E(x) in a range without capillary (cf. FIG. 4*c*: "reference surface"). Preferably, said correction is carried out for each capillary individually with a region without capillary directly next to said separate capillary. According to the invention, this is for example possible since the sample, contrary to measurement methods from the prior art, is moved preferably relative to the measurement system.

Figure 5:
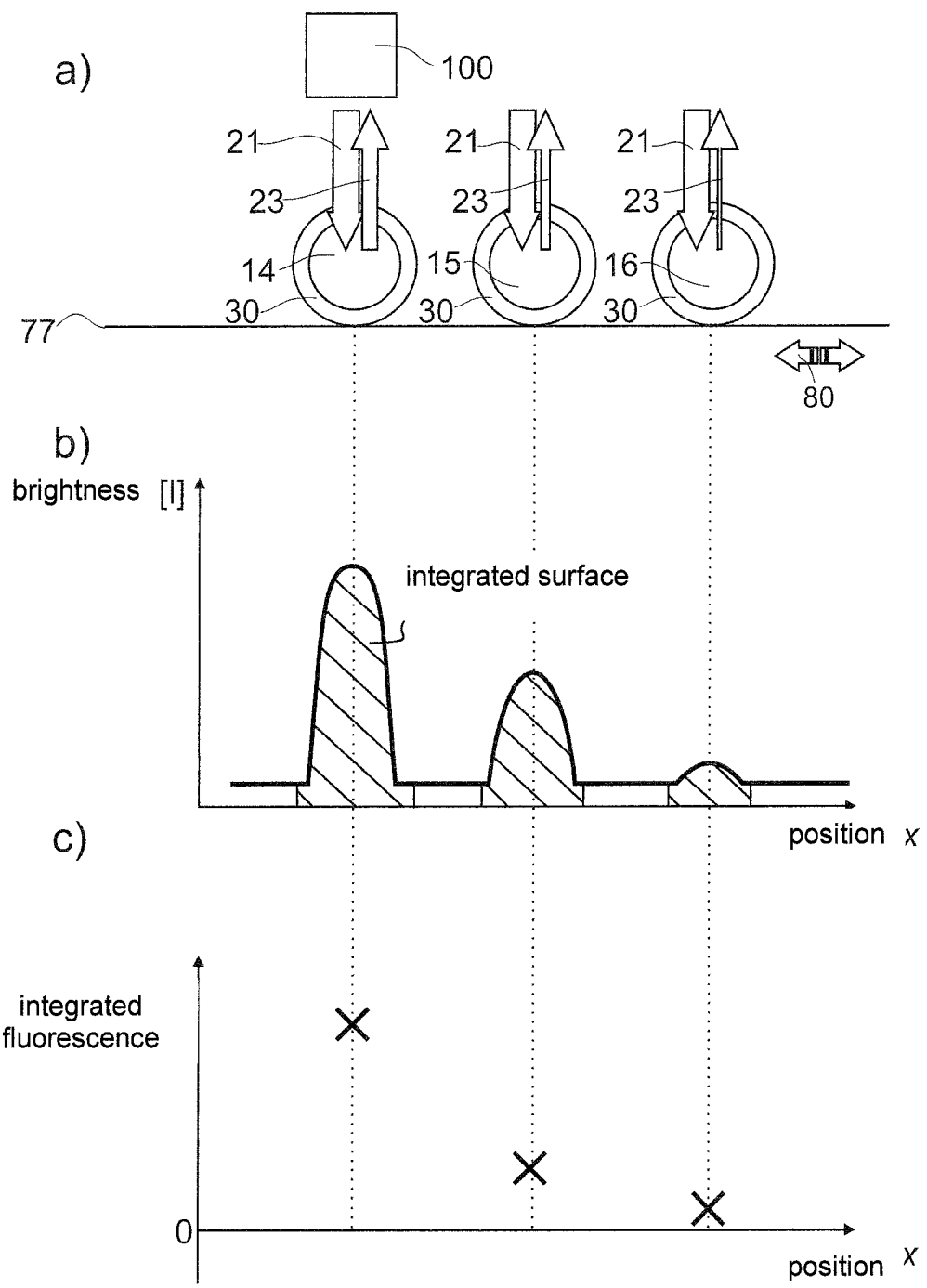
FIG. 5 shows an embodiment for evaluating the fluorescence measurement.

FIG. 5 exemplarily explains a possible processing of the measurement data from FIG. 3 using the example of three samples with high 14, average 15 and low 16 fluorescence.

The intensity of the fluorescence light which is emitted by the samples is shown in FIG. 5*b* dependent on the movement or the position of the detector 100 to the capillary. In order to determine a "fluorescence value", it is integrated over the value of the shifting 80 of the samples relative to the optical system (cf. FIG. 5*c*). The integration limits comprise preferably symmetrically one separate capillary. The integrated fluorescence intensity preferably corresponds to the measurement value of the fluorescence of a sample which is to be determined. It is also possible to measure the fluorescence intensities at two or more different wavelengths. In this case the ratio of the integrated fluorescence intensities is the measurement value "fluorescence ratio" which is to be determined.

Figure 6:
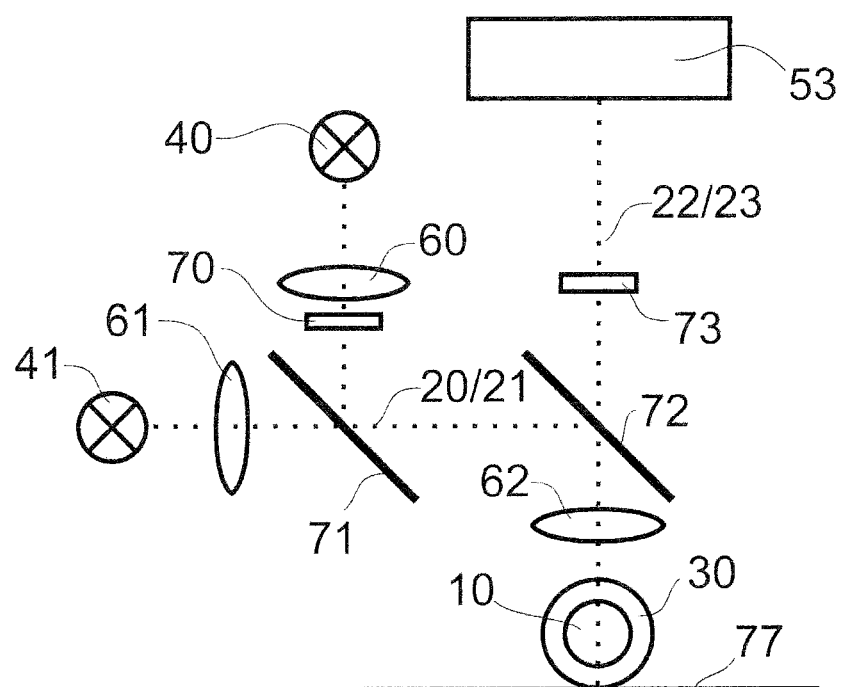
FIG. 6 shows an embodiment for measuring fluorescence and extinction simultaneously.

FIG. 6 shows an exemplary configuration of an inventive system for measuring fluorescence and extinction. Preferably, said measurement of fluorescence and extinction may be conducted after each other, almost simultaneously or simultaneously. A (first) light source 40, for example an LED, generates light radiation 21 with a (first) wavelength 21, which stimulates the emission of fluorescence radiation in the sample volume 10. The stimulation filter 70 suppresses possible radiation of the light source 40 in wavelengths ranges which are not desired. A (second) light source 41 generates light radiation 20 in a (second) wavelength range in which the sample volume 10 has only little absorption. The light of both light sources 40, 41 is preferably collimated with the optical lenses 60, 61 and combined to a collinear ray by a dichroic beam splitter.

The beam splitter 72 has a high reflectivity preferably in the (first) wavelength range 40. Furthermore, it is advantageous when the beam splitter 72 comprises a high transmission in the wavelength range of the fluorescence emission of the sample. It is also further preferred that the beam splitter 72 comprises partly a transmission and partly reflection in the wavelength range of the (second) light source 41. Said requirements are for example fulfilled by a dichroic beam splitter when the wavelength of 41 matches with the fluorescence emission of 10. In the more general case the beam splitter 72 is a trichroic beam splitter.

The beam splitter 72 reflects the light of the first and second wavelengths 20, 21 to the sample 10 in the capillary 30. The objective lens 62 focuses the irradiating light to the sample 10. The light of the first light source 40 generates in the sample 10 fluorescence radiation which is collimated by the lens 62. The light in the irradiating beam, which is generated by the second light source 41, arrives through the sample 10 and the capillary 30 at the surface 77, is reflected or backreflected and runs a second time through the sample 10 and the capillary 30.

The surface 77 is preferably made of a material having little fluorescence on its own and having high reflectivity in the wavelength range of the second source 41 in order to measure extinction. The reflected radiation is again collimated by the lens 62. Particles which are possibly present in the sample volume scatter the irradiating light so that only a smaller part of the originally irradiated light is absorbed by the objective lens 62. Thus, the intensity of the light which is reflected back to the lens 62 substantially depends on the concentration and dimension of the particles and thus on the extinction of the sample.

The filter 73 preferably suppresses the fluorescence excitation light of the (first) light source 40. The detector 53 measures, preferably in a wavelength-selective manner, the intensity of the ray of light coming from the sample. Preferably, the light of the second wavelength, i.e. the light which passes through the sample and is reflected back, as well as the fluorescence light, i.e. light of the fluorescence emission of the sample, are measured by the detector 53. Furthermore, wavelength-selectively means that the intensities at the different wavelengths may be determined preferably separately from each other.

Figure 7B:
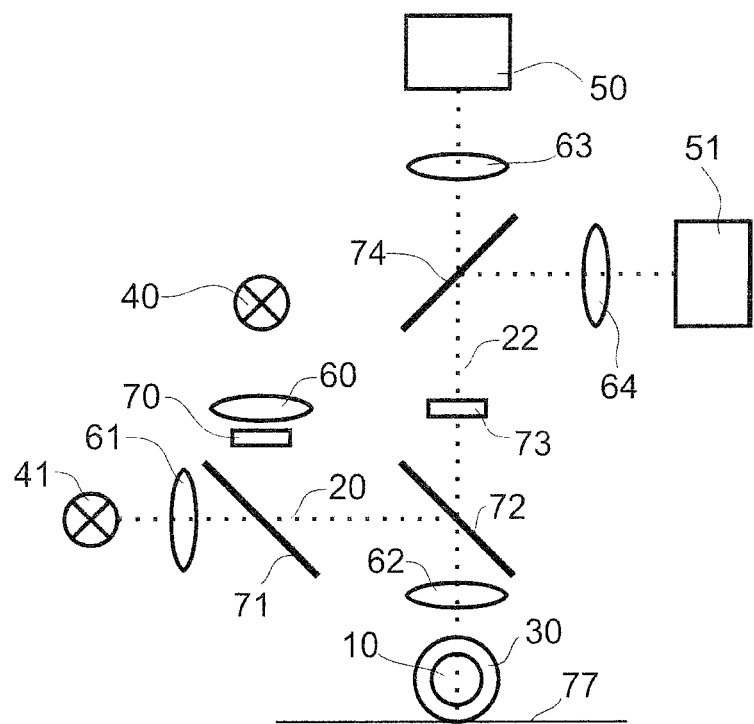
FIG. 7b shows the embodiment of FIG. 7a, however, with drawn-in path of extinction rays.
Figure 7A:
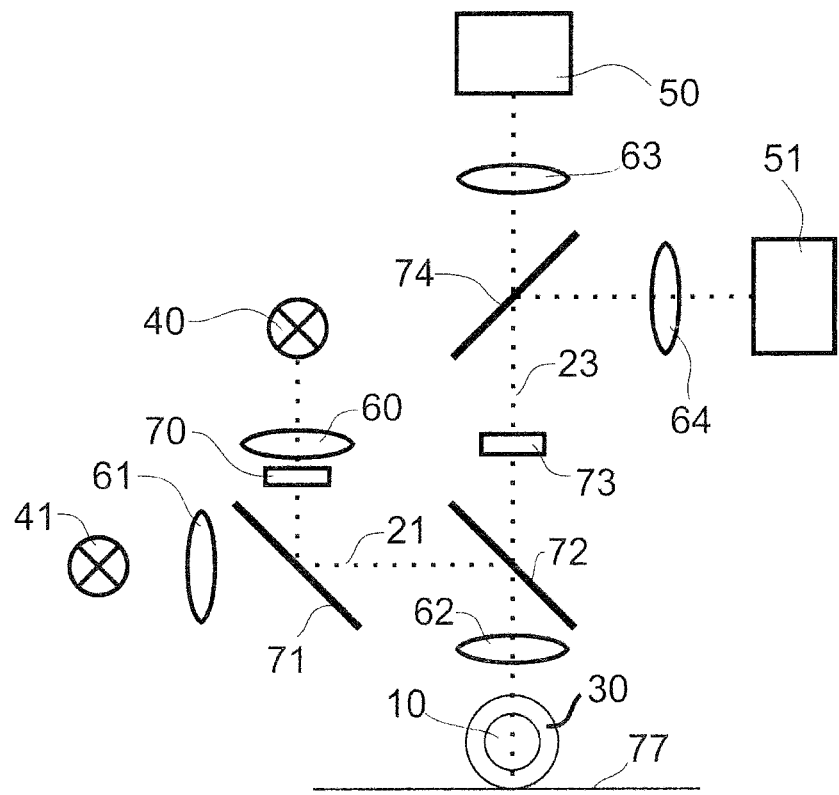
FIG. 7a shows an embodiment for the almost simultaneous measurement of fluorescence ratio and extinction with drawn-in path of fluorescence rays.

FIG. 7a) shows a further inventive embodiment of the system with drawn-in path of rays during fluorescence measurement. However, contrary to FIG. 6, the system has (at least) two detectors. Both detectors 50, 51 serve for the measurement of fluorescence intensity at two different wavelengths. For example, if 330 nm and 350 nm are chosen as detected wavelengths, the ratio of both signals provides information regarding the structure of macromolecules which are present in the sample volume 10.

In said embodiment the wavelength of the (second) light source 41 for the extinction measurement is in the range of the fluorescence emission of the sample 10. Thus, during the measurement of fluorescence the light source 41 should be switched off. A sequential or almost simultaneous measurement is generated due to a fast and alternating measurement of extinction and fluorescence. The time which passes between two data points of a measurement type has to be so short that the difference between two measured values is less than the measurement uncertainty of a measured value. Example: extinction of a highly concentrated sample changes at temperatures over 80° C. with approx. 0.2 mAU/s (milli absorption units/second). The measurement uncertainty with respect to the extinction is for example approx. 0.2 mAU. Correspondingly, extinction is measured preferably at least 1× per second and fluorescence also at least 1× per second. In said embodiment the bandpass 73 transmits one part of the fluorescence radiation 23, for example in the range of 320 nm to 360 nm. The beam splitter 74 separates the fluorescence radiation into two rays with wavelength ranges of for example 320 nm-340 nm and 340 nm-360 nm. The rays are bundled with the concentrator lenses 63, 64 onto both detectors 50, 51. The quotient of both measurement signals is the measured value to be determined.

FIG. 7b) shows the exemplary embodiment of the system of FIG. 7a), however, with drawn-in path of rays during the extinction measurement. The second light source 41 emits light radiation 20 which twice runs through the sample 10 after reflection at the base plate 77 and runs upwards as ray of light 22. In the sample 10 the intensity of the ray of light is diluted by scattering from the detection range. The wavelength of the (second) light source 41 preferably is in the transmission range of the filter 73. Depending on the wavelength of the light source 41 the light then disperses to both detectors 50, 51. Preferably, the wavelength is at approx. 350 nm so that the largest part of the light is measured by one single detector.

Figure 8B:
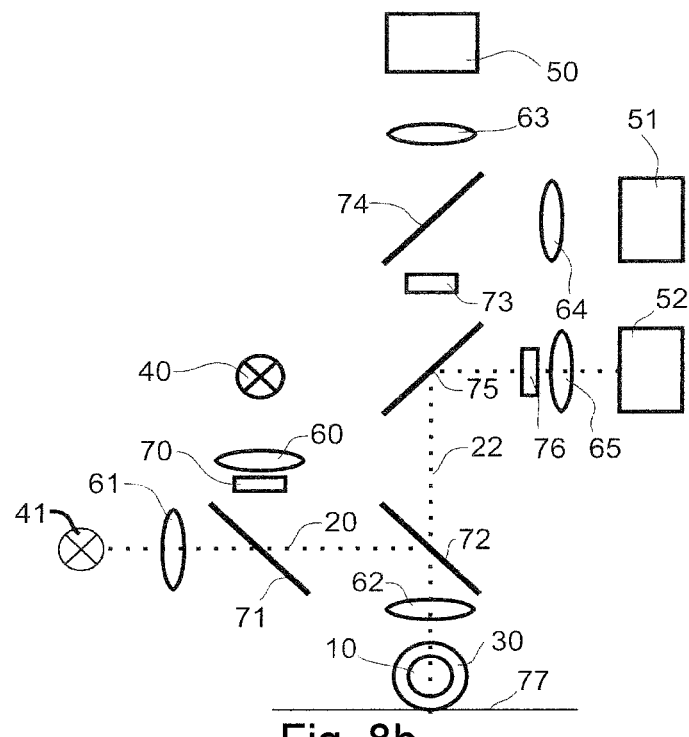
FIG. 8b shows the embodiment of FIG. 8a, however, with drawn-in path of extinction rays.
Figure 8A:
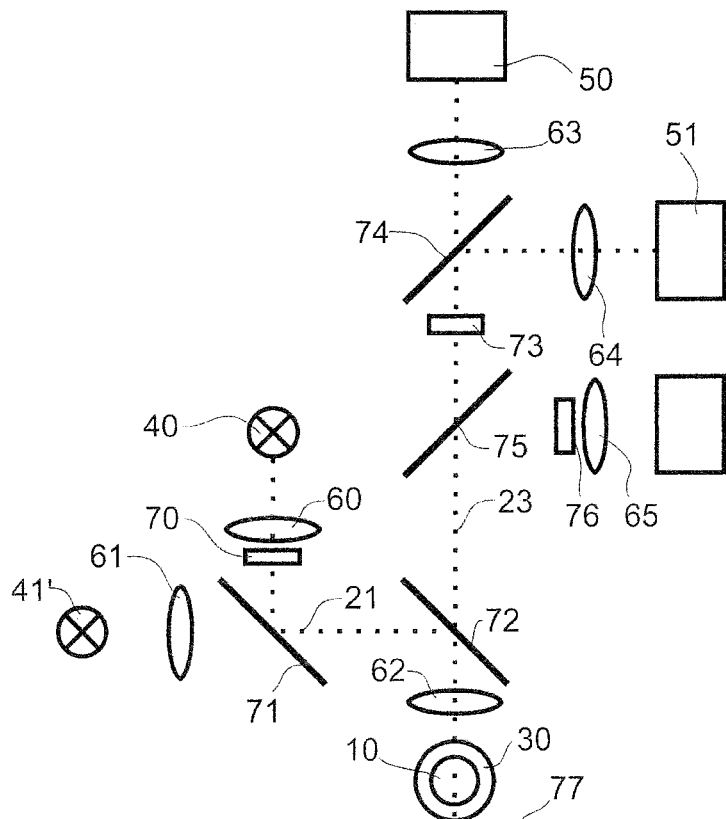
FIG. 8a shows a further embodiment for the simultaneous measurement of fluorescence ratio and extinction with drawn-in path of fluorescence rays.

FIG. 8a) shows an exemplary embodiment of the system of FIG. 6 which is expanded by an additional detection branch, compared with the embodiment in FIG. 7. The path of rays for the fluorescence, which corresponds to the path of rays in FIG. 7a, is drawn in. The additional dichroic beam splitter 75 is transparent in the wavelength range which is measured by the detectors 50, 51.

FIG. 8b) shows the system of FIG. 8a) with drawn-in path of rays for the extinction measurement. Compared to the system of FIG. 7, the wavelength range of the light source 41 lies outside the wavelength range which is measured by the detectors 50, 51, for example 380 nm. Thus, the light source 41 may be switched on during the measurement and it does not have to be switched between the measurement types fluorescence and extinction. The beam splitter 72 is partly transparent in the wavelength range of source 41. Ideally, the transmission/reflection ratio is 1:1.

The beam splitter 75 directs the light from the (second) light source 41 to the detector 52 after it has been diluted by extinction in the sample 10. The bandpass 76 preferably reduces the share in fluorescence light to the detector 52.

Due to said embodiment with three detectors 51, 52, 53 extinction and fluorescence ratio may be measured continuously and simultaneously. Furthermore, the sensitivity of the detector 52 may individually be adapted to the intensity of the radiation from the light source 41. The sensitivity of the detector may be adjusted for example significantly higher for a noise-reduced measurement of the extinction. In an advantageous embodiment the signals of the detectors are digitalized by a 24 bit analog digital converter (ADC) which may read in simultaneously all three detector channels, for example with a rate of 4 kHz.

Figure 9:
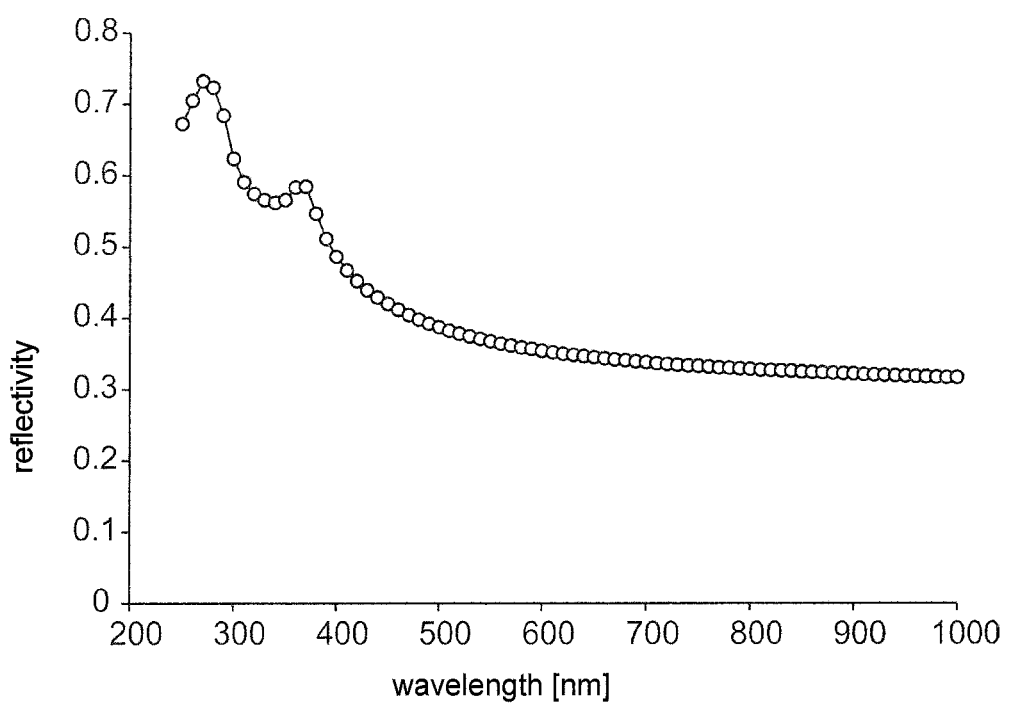
FIG. 9 shows the reflectivity of silicon.

FIG. 9 is a diagram in which the reflectivity is shown dependent on the wavelength for silicon. In particular, FIG. 9 shows the good reflectivity of silicon in the UV range, which is particularly preferred so that the light intensity reflected to the detector is as high as possible during the extinction measurement. In particular, a high light intensity enables a measurement having little noise. Further advantageous properties of silicon are that the used wavelengths have almost no fluorescence themselves, that they may be mechanically manufactured easily and that they have high chemical resistance.

Figure 10:
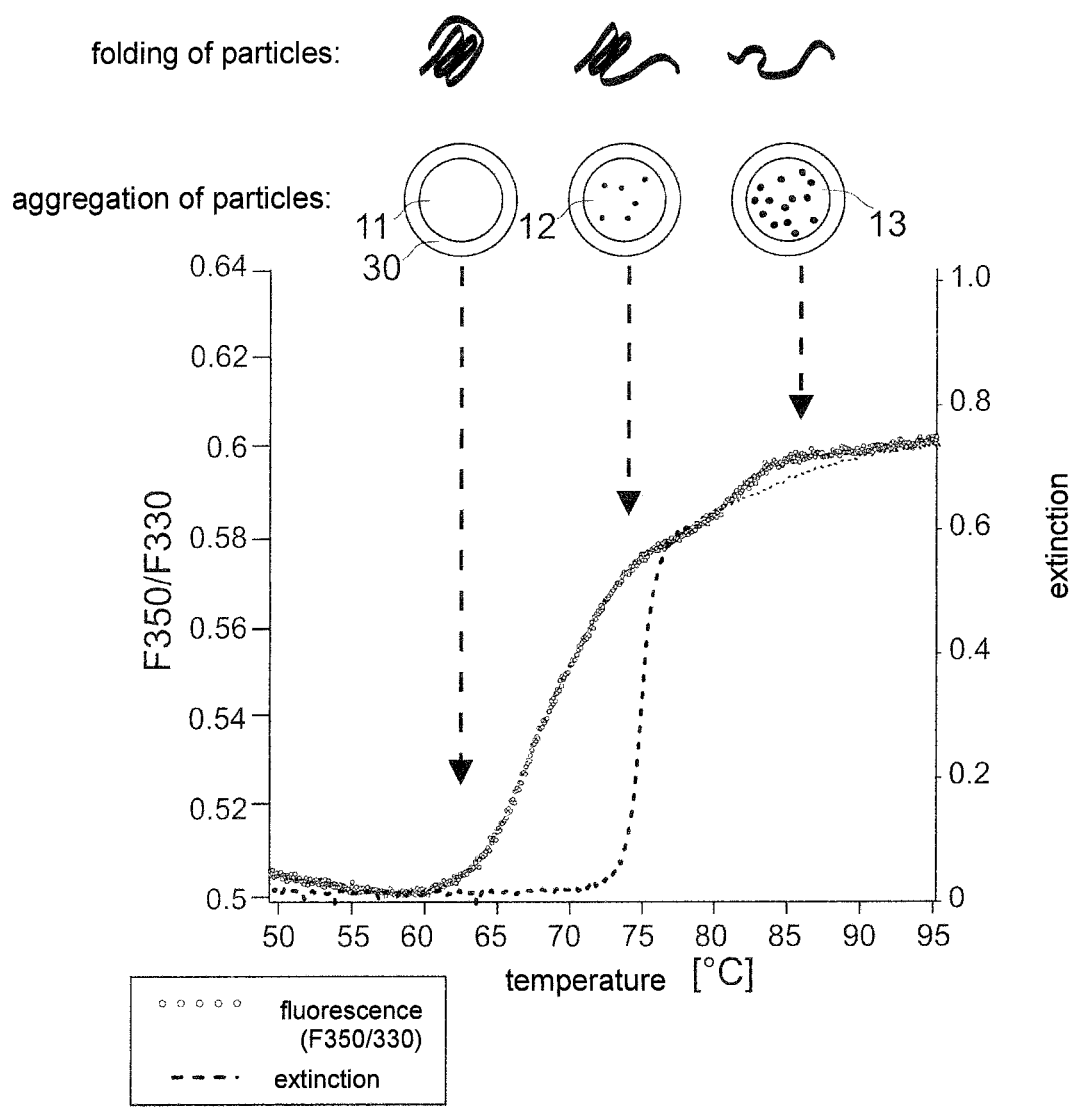
FIG. 10 shows a measurement example for simultaneously detecting the intramolecular unfolding by means of fluorescence and the intermolecular aggregation by means of extinction of an antibody.

FIG. 10 exemplarily shows a measurement with the inventive system described in FIG. 6. The unfolding of proteins dependent on the temperature as well as the aggregation of an antibody dependent on the temperature is shown. In the shown example the unfolding of one of the sub-units of the antibody starts already at 60° C., which is characterized by a characteristic change in the fluorescence ratio between the emission at 350 and 330 nm. An increase of the aggregation and thus in the extinction, is observed only from 73° C. onwards, which suggests that an unfolding of the thermally more instable protein domain does not contribute to the aggregation of the antibody.

Figure 11:
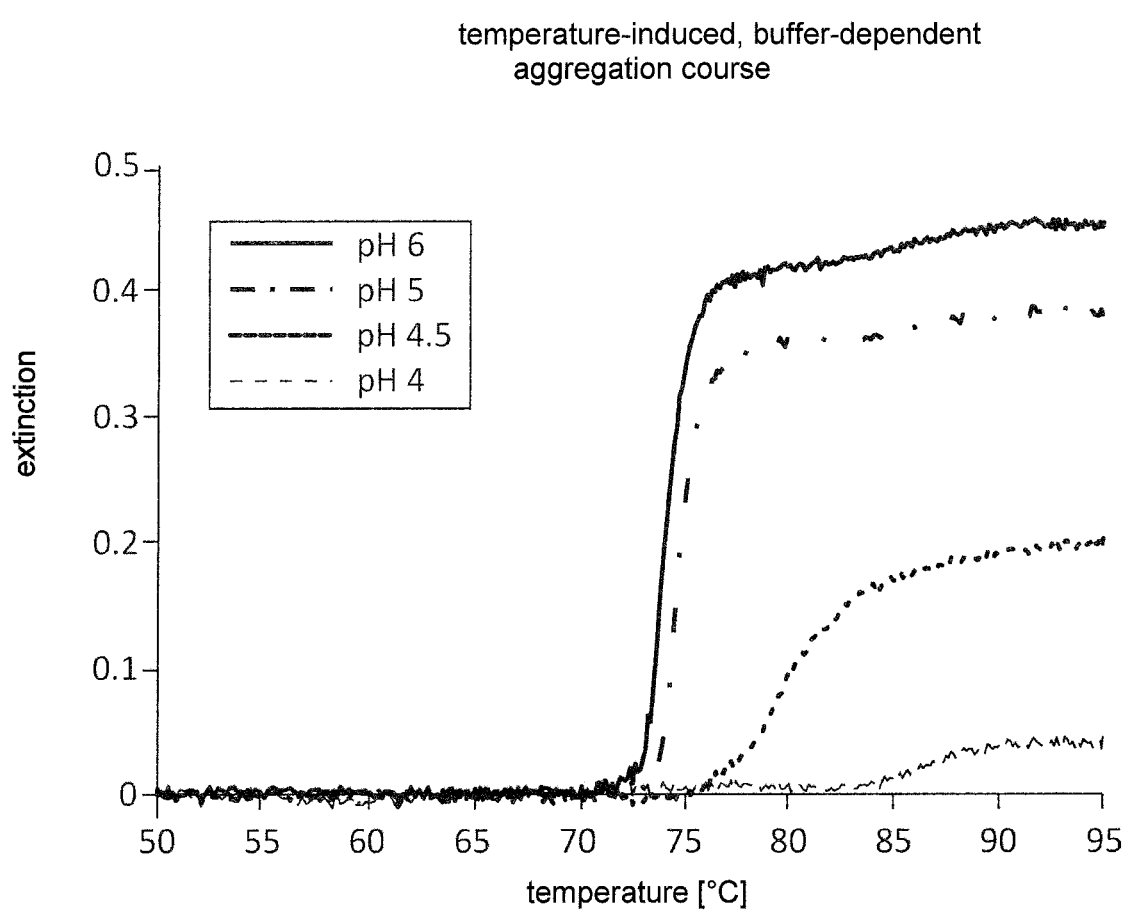
FIG. 11 shows a measurement example of the increase in aggregation of an antibody dependent on the temperature in different buffers.

FIG. 11 exemplarily shows the measurement of extinction of an antibody (rituximab) having a substance concentration of 1 mg/ml in 25 mM acetate buffer at different pH values between pH4 and pH6. 10 μl of the solution was heated in each capillary from 50 to 95° C. with a heating rate of 1° C./min. An increase in the extinction can be observed at increased temperatures >72° C., which may be explained by aggregation. The extent of the extinction increase depends on the pH value of the solution, wherein lower pH values counteract the temperature-induced aggregation. This is characterized on the one hand by a late start of the extinction increase ("aggregation-onset temperature") and on the other hand by a total lower maximum extinction.

Figure 12:
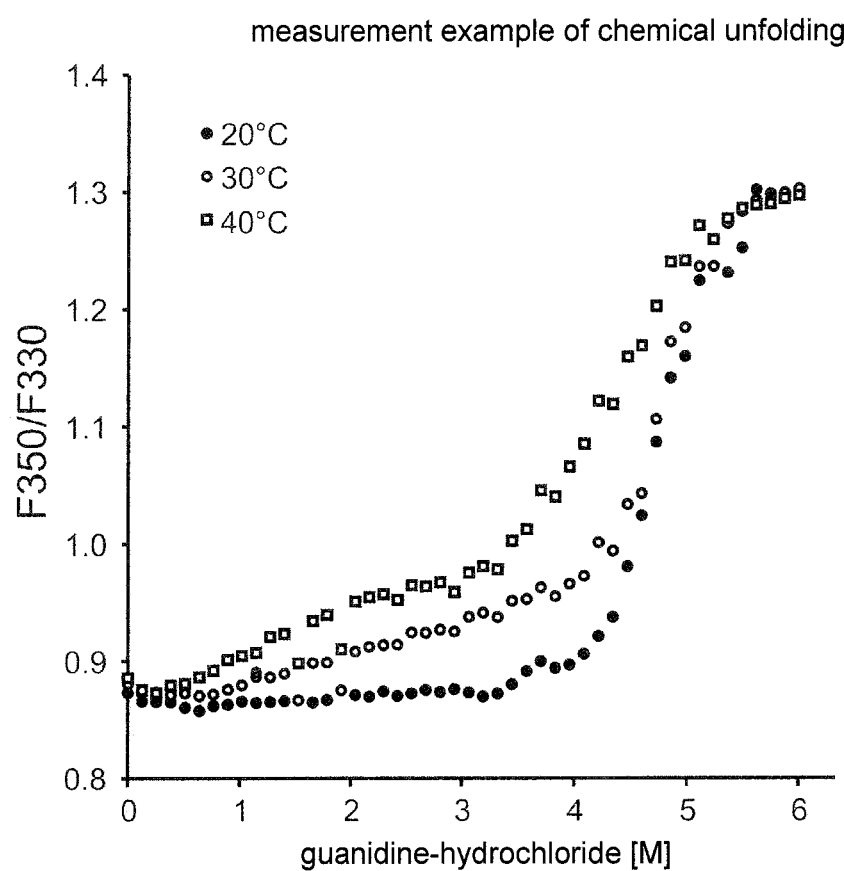
FIG. 12 shows a measurement example for the detection of protein stability at different temperatures by chemical unfolding.

FIG. 12 exemplarily shows the analysis of the chemical stability of the protein lysozyme in 10 mM citrate buffer pH4 at different guanidine-hydrochloride concentrations. 1 mg/ml lysozyme was prepared with increasing guanidine-chloride concentration in 48 solutions and 10 μl of each solution was filled into capillaries, said capillaries arranged and fixed on the capillary array and subsequently each capillary scanned at 20° C., 30° C. and 40° C. Subsequently, the obtained fluorescence ratios are set in relation to increasing guanidine concentrations. In particular, the fluorescence ratio shows in all samples a sigmoidal increase when the guanidine concentration increases, which is directly proportional to the portion of unfolded protein. When the temperature increases, the protein more and more destabilizes, which is characterized by a shifting of the data points to lower guanidine concentrations.

Figure 13:
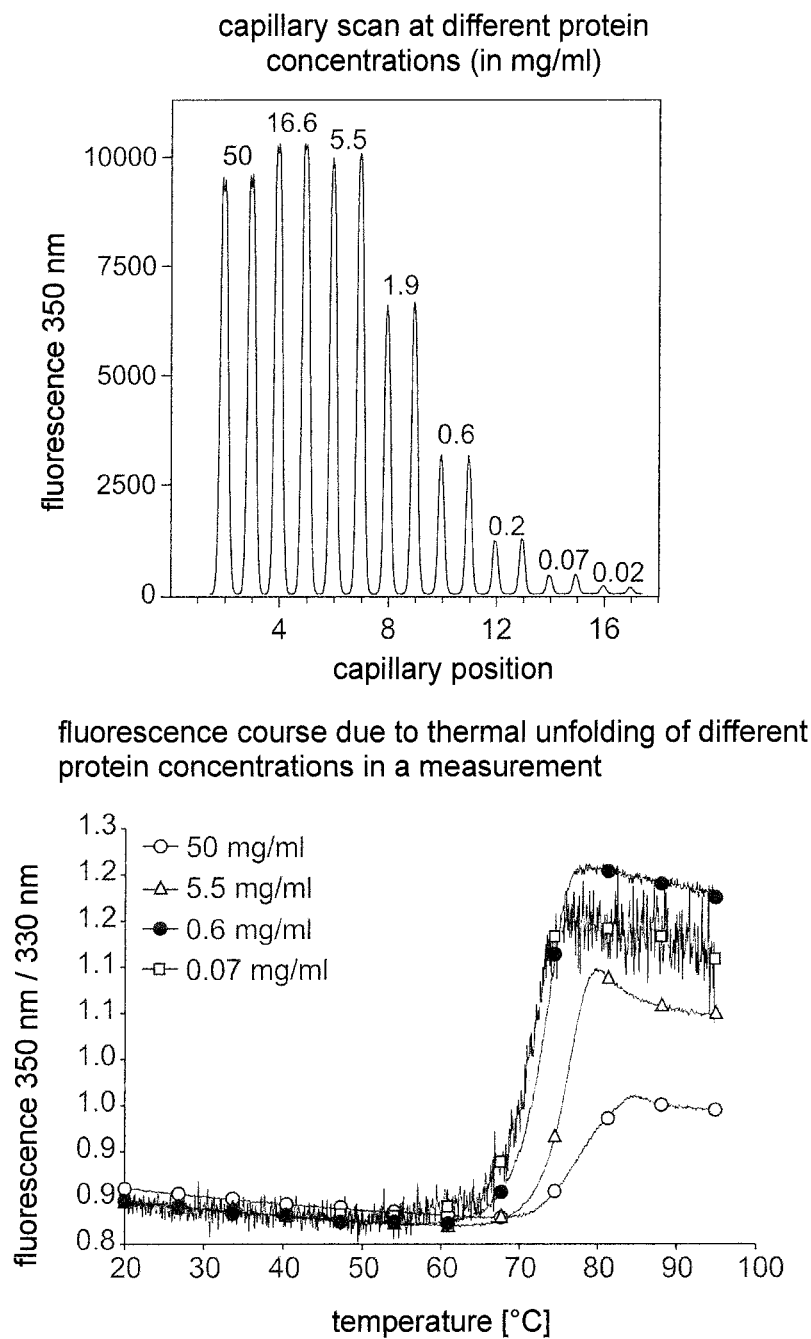
FIG. 13 shows an exemplary measurement for the demonstration of the dynamic range of the fluorescence optics when different protein concentrations between 50 mg/ml and 2 µg/ml are used.

FIG. 13 shows the exemplary measurement of the protein streptavidin in PBS, pH 7.3, at different substance concentrations of 50 mg/ml to 7 μg/ml. The capillary scan illustrates the different fluorescence intensities in the capillaries. The upper diagram shows the capillary scan at the beginning of the measurement of the thermal unfolding. All concentrations are measured as duplicates. The height of the peaks corresponds to the fluorescence intensity in the capillaries at an emission wavelength of 350 nm. The decrease of the fluorescence at high streptavidin concentration can be explained by the inner filter effect, which is generated by the strong absorption of the excitation light and reduced intrusion depth caused thereby (thus lower fluorescence). The lower diagram shows the course of the temperature of the fluorescence ratio at 350 nm and 330 nm. Said unfolding curves show that unfolding profiles have been recorded for all concentrations. At all concentrations a clear unfolding process may be recognized. The melting transition is shifted to higher temperatures at high streptavidin concentrations, which is due to an intramolecular stabilization of the protein.

Figure 14:
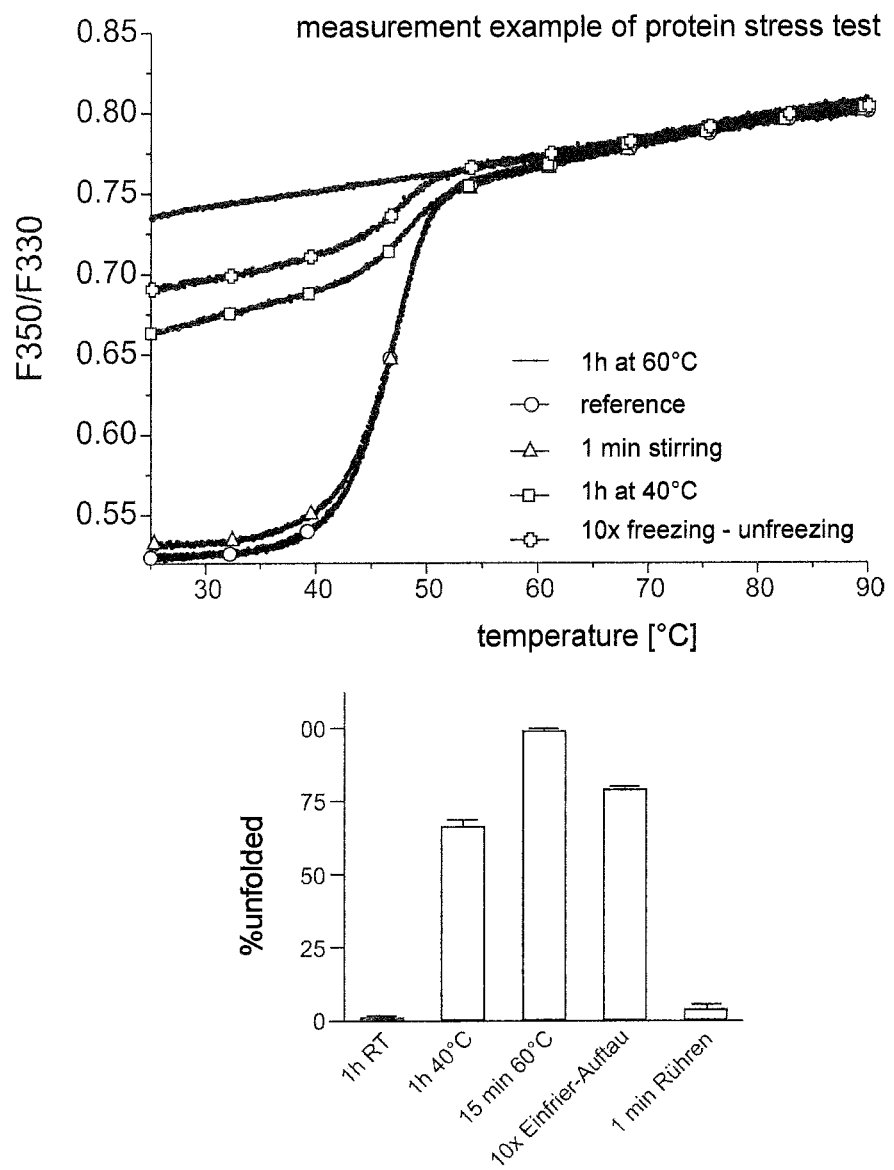
FIG. 14 shows an exemplary measurement for the quality control of proteins by forced degradation tests.

FIG. 14 shows exemplary data of a forced degradation test for the protein MEK1-kinase. A solution with a concentration of 1 mg/ml in 50 mM hepes pH 7.4, 150 mM NaCl and 2 mMDTT was prepared and divided into 5 aliquots à 50 µl. While an aliquot was stored at 4° C. and served as reference, the remaining aliquots were exposed to different conditions—incubation at increased temperature, freezing-unfreezing cycles, strong stirring. Subsequently, all samples were filled into capillaries, placed on the capillary array and pressed on, and the thermal unfolding detected at a heating rate of 1° C./min from 25° C. to 90° C. via the fluorescence. The upper diagram shows the unfolding curves of the samples. Depending on the previous treatment, the starting levels of the unfolding curves are different, which suggests different shares of already unfolded protein. The lower diagram shows a quantification of the share of unfolded protein in %, wherein the sample of the 4° C. incubation unfolds as 0% and the sample after 15 minutes of incubation at 60° C. was used as reference.

Figure 15:
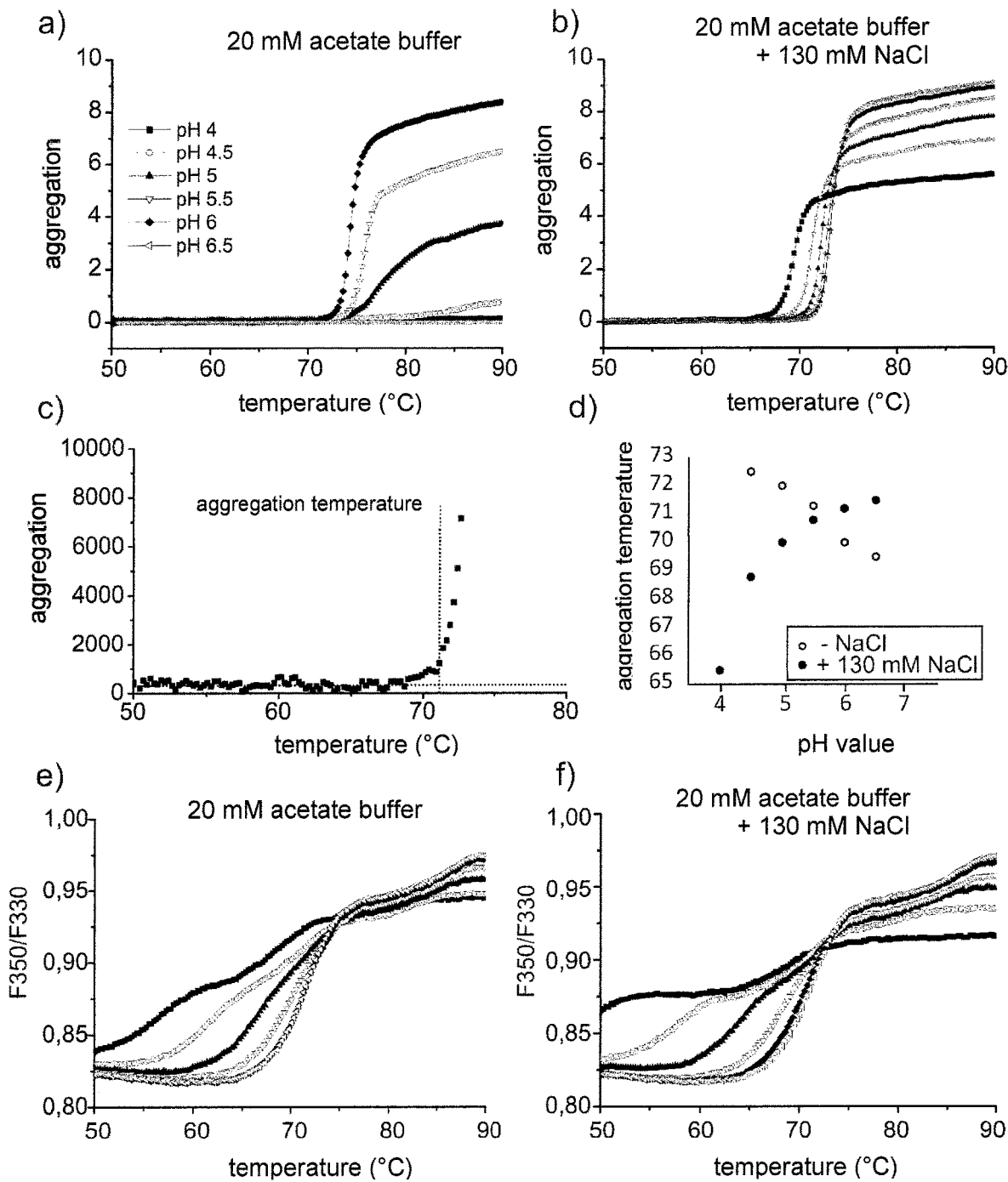
FIG. 15 shows exemplary measurement data for the buffer screening for optimum storage conditions of an antibody.

FIG. 15 shows exemplary data of a buffer screening for the identification of optimum conditions for the storage of antibodies. A monoclonal antibody was stored at a concentration of 5 mg/ml in acetate buffer with different pH values as well as in the absence and the presence of 130 mM NaCl. 10 µl of each antibody solution was subsequently filled into glass capillaries and the temperature-dependent unfolding of proteins was measured via the change in fluorescence and the temperature-dependent aggregation was measured via the increase of extinction at a heating rate of 1° C./min FIGS. 15a) and b) show the temperature-dependent increase in the aggregation. In the shown case the total aggregation increases with increasing pH value, which is characterized by higher amplitudes in the aggregation signal. The addition of physiological salt concentrations leads to a further increase in the aggregation at all pH values (b). Figs. c) and d) exemplarily show the determination of the aggregation-onset temperature, which corresponds to the lowest temperature at which a significant increase of the extinction in relation to the base line is observed. Fig. d) exemplarily shows the different dependency of the aggregation temperature on the pH value and the salt concentration. Figs. e) and f) show fluorescence data which are recorded, according to the invention, simultaneously with the aggregation data shown in FIGS. 15a) and b). With an increasing pH value of the solution, the antibody shows higher thermal stability. Furthermore, NaCl has negative effects on thermal stability, which can be recognized by means of an unfolding of the proteins at lower temperatures. By comparable experiments conditions may be detected under which the thermal stability of a protein, for example an antibody, is maximal and the aggregation is minimal.

FIG. 16 shows an exemplary absorption spectrum of a protein.

The invention also comprises the accurate or exact expressions, features, numeric values or ranges etc when said expressions, features, numeric values or ranges are before or subsequently named with terms like "approximately, about, substantially, generally, at least" etc (i.e. "approximately 3 should also comprise "3" or "substantially radial" should also comprise "radial").

LIST OF REFERENCE SIGNS

10: sample
11: sample without scattering/aggregating particle
12: sample with some scattering/aggregating particles
13: sample with strongly scattering/aggregating particles
14: sample with many fluorescent particles
15: sample with some fluorescent particles
16: sample with few fluorescent particles
20: irradiated light for the extinction measurement
21: excitation light for fluorescence
22: reflected light
23: emission light fluorescence
24: scattered light in specific scattering angle Q
25: "undesired" scattered light
26: "undesired" reflected scattered light
30: capillary
40: light source for fluorescence excitation
41: light source for extinction
50: detector 1 (fluorescence and extinction)
51: detector 2 (fluorescence and extinction)
52: detector 3 (extinction)
53: detection system
60: collimator lens for 40
61: collimator lens for 41
62: objective lens
63: concentrator lens for 50
64: concentrator lens for 51
65: concentrator lens for 52
70: excitation filter for 40
71: beam splitter for the combination of 40+41
72: beam splitter for separating excitation and fluorescence
73: fluorescence emission filter
74: beam splitter for separating fluorescence
75: beam splitter for separating fluorescence and extinction
76: extinction filter
77: reflecting, non-fluorescent surface, for example silicon surface
80: running directions of the capillary array
90: groove, furrow, ditch, recess
91: edge region
100: inventive alternative for detection
200: detection optics for scattered light according to the prior art

The invention claimed is:

1. A method for optically measuring at least the stability and the aggregation of particles in a liquid sample, which is in a sample container, wherein the method comprises the following steps:
    irradiating the sample with light of at least a first wavelength, to fluorescently excite the particles,
    irradiating the sample with light of at least a second wavelength to examine the scattering of the particles,
    measuring the fluorescence light emitted by the sample; and
    measuring the extinction light at the second wavelength, wherein the irradiated light of the second wavelength runs through the sample container, is reflected back, runs again through the sample container in opposite direction and exits as extinction light, wherein the stability is measured on the basis of the measured fluorescence light and the aggregation on the basis of the measured extinction light;

wherein the sample container is shifted during a measuring period relatively to the irradiated light of the first and/or second wavelength and/or to the detector and is driven back and forth several times; and wherein a plurality of sample containers or a plurality of capillaries are scanned by said relative movement.

2. The method according to claim 1, wherein the fluorescence light and the extinction light are measured with a common optical system.

3. The method according to claim 1, wherein the irradiation of the sample
   i) is not conducted simultaneously with the first and second wavelengths; or
   ii) the irradiation with the second wavelength is conducted continuously, whereas the irradiation with the first wavelength is conducted intermittently.

4. The method according to claim 1, wherein the fluorescence light and the extinction light are measured simultaneously.

5. The method according to claim 1, wherein
   i) the extinction light and the fluorescence light are measured by a common detector;
   ii) the extinction light is measured by a first detector and/or a second detector and fluorescence light of a first fluorescence wavelength is measured by the first detector and fluorescence light of a second fluorescence wavelength is measured by the second detector; or
   iii) the extinction light is measured by a first detector, fluorescence light of a first fluorescence wavelength is measured by a second detector and fluorescence light of a second fluorescence wavelength is measured by a third detector.

6. The method according to claim 1, wherein the sample container is a capillary.

7. The method according to claim 1, wherein the sample container is tempered, preferably rests on a tempering element and is tempered by a contact, wherein the tempering element further preferably reflects back the irradiated light of the second wavelength, again runs through the sample container in opposite direction and exits as extinction light.

8. The method according to claim 7, wherein the tempering element is made of a material
   i) which has little autofluorescence <1%, and/or
   ii) which has a high reflectivity >30% in the wavelength range of the second wavelength.

9. The method according to claim 1, wherein at the surface of the tempering element at least one groove is configured, the sample container is arranged above the groove and the irradiated light of the second wavelength is reflected back from the bottom of the groove.

10. The method according to claim 9, wherein the groove has a width between 1-10 mm and a depth of more than half of the coherence length of the light of the second wavelength.

11. The method according to claim 1, wherein
    i) a fluorescence value is determined by integrating the intensity of the fluorescence light via the shifting and/or
    ii) an extinction value is determined by integrating the intensity of the extinction light via the shifting.

12. The method according to claim 1, wherein during a measuring period
    i) in order to determine the thermal stability the temperature of the samples is changed, preferably increased;
    ii) in order to determine chemical stability the concentration of denaturants in different liquid samples is chosen differently; and/or
    iii) in order to determine stability in terms of time the sample is kept at a substantially constant temperature via a time period of more than one hour.

13. The method according to claim 1, wherein during a measuring period a plurality of sample containers and/or the optical system are continuously driven back and forth several times and the measurements of the fluorescence light and/or the extinction light are conducted during the movement.

14. The method according to claim 1, wherein the second wavelength is chosen such that less than 1%, 0.1%, 0.05% is absorbed by the sample or the particles in the sample.

15. The method according to claim 1, wherein the light of the first wavelength and the light of the second wavelength are united to a collinear ray which is irradiated into the sample container.

16. The method according to claim 1, wherein the extinction light of the second wavelength, which is reflected back and leaves the sample container in the opposite direction to the irradiation direction, deviates from the irradiation direction 5° at most.

17. An apparatus for the optical measurement of the stability and the aggregation of particles in a liquid sample, which is located in a sample container, in particular according to any one of the preceding claims, wherein the apparatus comprises:
    a first light source for irradiating light of a first wavelength into the sample container to fluorescently excite the particles to be examined,
    a second light source for irradiating light of a second wavelength into the sample container to measure the scattering of the particles,
    a first detector for measuring the excited fluorescence light which is radiated from the sample,
    a second detector for measuring extinction light at the second wavelength wherein the irradiated light of the second wavelength runs through the sample container, is reflected back, runs again through the sample container in the opposite direction and exits as extinction light; and
    an evaluation means which determines the stability of the particles based on the measured fluorescence light and which determines the aggregation of the particles based on the measured extinction light;
    wherein the sample container is configured to shift during a measuring period relative to the irradiated light of the first and/or second wavelength and/or to the detector and is configured to be driven back and forth several times; and
    wherein a plurality of sample containers or a plurality of capillaries are configured to be scanned by said relative movement.

18. The apparatus according to claim 17 comprising a tempering element with a reflecting surface at which the irradiated light of the second wavelength is reflected back, and
    wherein the apparatus is preferably configured to arrange at least one sample container on the surface for measurement purposes.

19. The apparatus according to claim 18, wherein the at least one sample container is a capillary.

20. The apparatus according to claim 18, wherein the reflective surface consists of silicon.

21. The apparatus according to claim 18, wherein at least one groove is configured at the surface of the tempering element, the sample container is arranged above the groove and the irradiated light of the second wavelength is reflected back from the bottom of the groove.

22. The apparatus according to claim 21, wherein the groove has a width between 1-10 mm and a depth of more than half of the coherence length of the light of the second wavelength.

23. The use of an apparatus according to claim 17 for conducting a method for optically measuring at least the stability and the aggregation of particles in the liquid sample, which is in the sample container, wherein the method comprises the following steps:

irradiating the sample with the light of at least the first wavelength, to fluorescently excite the particles, irradiating the sample with the light of at least the second wavelength to examine the scattering of the particles, measuring the fluorescence light emitted by the sample; and measuring the extinction light at the second wavelength, wherein the irradiated light of the second wavelength runs through the sample container, is reflected back, runs again through the sample container in opposite direction and exits as extinction light, wherein the stability is measured on the basis of the measured fluorescence light and the aggregation on the basis of the measured extinction light;

wherein the sample container is shifted during a measuring period relatively to the irradiated light of the first and/or second wavelength and/or to the detector and is driven back and forth several times; and wherein the plurality of sample containers or the plurality of capillaries are scanned by said relative movement.

* * * * *